United States Patent
Lindh, Sr. et al.

(10) Patent No.: US 10,213,197 B2
(45) Date of Patent: Feb. 26, 2019

(54) SUTURE HAVING A RESTRAINING ELEMENT AT AN END AND METHOD AND USE THEREOF

(71) Applicant: Ethicon, Inc., Somerville, NJ (US)

(72) Inventors: David C. Lindh, Sr., Flemington, NJ (US); Robert A. Rousseau, Ottsville, PA (US); Darrell J. Lindh, East Wakefield, NH (US)

(73) Assignee: Ethicon LLC, Guaynabo, PR (US)

( * ) Notice: Subject to any disclaimer, the term of this patent is extended or adjusted under 35 U.S.C. 154(b) by 380 days.

(21) Appl. No.: 14/887,496

(22) Filed: Oct. 20, 2015

(65) Prior Publication Data

US 2016/0106422 A1 Apr. 21, 2016

Related U.S. Application Data

(60) Provisional application No. 62/066,597, filed on Oct. 21, 2014.

(51) Int. Cl.
| | | |
|---|---|---|
| *A61B 17/04* | (2006.01) | |
| *A61L 17/00* | (2006.01) | |
| *A61B 17/06* | (2006.01) | |
| *A61B 17/00* | (2006.01) | |

(52) U.S. Cl.
CPC .... *A61B 17/06166* (2013.01); *A61B 17/0401* (2013.01); *A61B 2017/00526* (2013.01); *A61B 2017/0404* (2013.01); *A61B 2017/06176* (2013.01)

(58) Field of Classification Search
CPC .......... A61B 17/06166; A61B 17/0401; A61B 17/0485; A61B 2017/06176; A61B 2017/00526; A61B 2017/0417; A61B 2017/0464; A61B 2017/0619; A61B 2017/06057

See application file for complete search history.

(56) References Cited

U.S. PATENT DOCUMENTS

| | | | |
|---|---|---|---|
| 5,489,294 A | * | 2/1996 | McVenes .......... A61N 1/0587 607/120 |
| 5,964,765 A | | 10/1999 | Fenton, Jr. et al. |
| 6,010,525 A | | 1/2000 | Bonutti et al. |
| 6,159,234 A | | 12/2000 | Bonutti et al. |
| 6,217,591 B1 | | 4/2001 | Egan et al. |
| 6,848,152 B2 | | 2/2005 | Genova et al. |

(Continued)

FOREIGN PATENT DOCUMENTS

| | | |
|---|---|---|
| EP | 2 305 130 A2 | 4/2011 |
| WO | WO 2012/004758 | 1/2012 |
| WO | WO 2015/069042 | 5/2015 |

OTHER PUBLICATIONS

European Search Report and Written Opinion dated Jul. 25, 2017 for Application No. EP16204074.5, 12 pgs.

(Continued)

*Primary Examiner* — Jonathan Miles
*Assistant Examiner* — Mohamed Gabr
(74) *Attorney, Agent, or Firm* — Frost Brown Todd LLC

(57) ABSTRACT

Polymeric fibers, and apparatuses for and methods of processing such fibers to be useful as sutures, where at least one end of a fiber includes a termination feature. The termination feature is formed through the application of energy to a coiled region of the fiber.

20 Claims, 16 Drawing Sheets

(56) References Cited

U.S. PATENT DOCUMENTS

| | | | |
|---|---|---|---|
| 8,100,940 | B2 | 1/2012 | Leung et al. |
| 8,297,330 | B2 | 10/2012 | O'Neill |
| 8,323,316 | B2 | 12/2012 | Maiorino et al. |
| 8,333,788 | B2 | 12/2012 | Maiorino |
| 8,403,017 | B2 | 3/2013 | Maiorino et al. |
| 9,023,081 | B2 | 5/2015 | Maiorino et al. |
| 9,038,688 | B2 | 5/2015 | Maiorino et al. |
| 9,533,446 | B2 | 1/2017 | Rousseau |
| 2003/0149447 | A1 | 8/2003 | Morency et al. |
| 2005/0216059 | A1 | 9/2005 | Bonutti et al. |
| 2005/0267531 | A1* | 12/2005 | Ruff .................. A61B 17/04 606/228 |
| 2006/0116718 | A1 | 6/2006 | Leiboff |
| 2009/0248067 | A1 | 10/2009 | Maiorino |
| 2011/0079341 | A1* | 4/2011 | O'Neill ............... B29C 65/08 156/73.1 |
| 2014/0025111 | A1 | 1/2014 | Bonutti et al. |

OTHER PUBLICATIONS

International Search Report and Written Opinion dated Apr. 19, 2016 for Application No. PCT/US2015/056335, 15 pgs.
International Search Report and Written Opinion dated Jul. 10, 2017 for Application No. PCT/US2016/065854, 20 pgs.

\* cited by examiner

SUTURE HAVING A RESTRAINING ELEMENT AT AN END AND METHOD AND USE THEREOF

This application claims priority to provisional U.S. Pat. App. No. 62/066,567, filed Oct. 21, 2014.

FIELD

This invention relates, in general, to the method of producing features on polymer fibers, more particularly on a non-needled end of a surgical suture device through the application of energy, radiofrequency, heat, or ultrasonic energy. More particularly, the suture devices are self-retaining suture devices. The invention further relates to such devices and methods of using the devices.

BACKGROUND

Various surgical methods employing sutures have been used in the past for closing or binding together wounds in human or animal tissue, such as skin, muscles, tendons, internal organs, nerves, blood vessels, and the like. More specifically, the surgeon may use a surgical needle with an attached conventional suture (which can be a smooth monofilament or can be a multi-filament) to pierce the tissue alternately on opposing faces of the wound and thus sew the wound closed. Whether the wound is accidental or surgical, loop stitching is the method often used, especially for surface wounds. The surgical needle is then removed and the ends of the suture are tied, typically with at least three overhand throws to form a knot.

Since the time of their conception, self-retaining sutures (sometimes referred to as barbed sutures), which are generally of the same materials as conventional sutures, have offered numerous advantages over closing wounds with conventional sutures. A self-retaining suture includes an elongated body that has one or more spaced retainers, which project from the body surface along the body length. The retainers are arranged to allow passage of the self-retaining suture in one direction through tissue but resist movement of the self-retaining suture in the opposite direction. Thus, the main advantage of self-retaining sutures has been the provision of a non-slip attribute. Accordingly, self-retaining sutures do not have to be knotted at the completion of the stitch, the requirement for a surgical follower to maintain tension on a continuous stitch, as is done in the application of conventional sutures, is also eliminated. However, like a conventional suture, a self-retaining suture may be inserted into tissue using a surgical needle.

While the retainers provide the strength necessary to prevent the fiber from slipping backwards and eliminates the need for tying a knot at the termination point of the stitch, the initial placement of the stitch may require the use of some means to anchor the suture in the local tissue. In response to this need, stitch initiation features have been incorporated into some self-retaining devices. Stitches may be initiated through the creation of a typical surgeon's knot or through the addition of clips or other mechanical clamping devices appended to the suture. Stitches may be initiated through the use of integral looped ends, tabs, buttons and reverse retainer elements. However, many of these anchoring means suffer from defects or are burdensome or costly to prepare, and thus the present invention seeks to provide an improved anchoring means.

For example, U.S. Patent Publication No. 2005/0267531 discloses a barbed suture device that is produced with a variety of anchoring elements attached to the non-needled end of the device. However, preparing these anchoring elements requires multiple secondary operations with great precision in the production of the anchors and the subsequent attachment to the fiber. This increased demand for secondary operations increases the cost to produce the device. U.S. Patent Publication No. 2009/0248067, issued as U.S. Pat. No. 8,932,327 on Jan. 13, 2015, discloses an anchoring device with a looped end with barbed type projections, while U.S. Pat. No. 8,403,017 similarly discloses a suture having a looped end.

U.S. Patent Publication No. 2006/0116718, now abandoned, discloses a prosthetic screen tacking device that is produced with a perpendicular foot at one end, while U.S. Pat. No. 5,964,765 discloses a single-piece soft tissue fixation device that includes an elongated element terminating in a tip at one end and a receptacle at the other end which can be bonded with each other in a welded joint. The device is made of a heat-bondable, biocompatible material that can be ultrasonically or thermally welded. The tip and receptacle of the device can be textured or contoured or otherwise complementarily configured to promote mutual engagement prior to and during bonding. It should be noted, that the receptacle component is not intended to provide the stitch initiation functionality, but rather to provide a replacement for a knot with a welded joint of the looped suture. Producing these geometries, however, is difficult.

U.S. Patent Publication No. 2003/0149447, now abandoned, discloses a barbed suture device that is produced with a stopper on the non-needled end. It is proposed that the device can be produced through injection molding, cutting ribbon or stamping ribbon stock to produce the desired shapes. These methods, including the use of injection molding, however, limits options of materials given the required melt viscosity, and through any of these methods, may ultimately result in weaker sutures. U.S. Pat. No. 8,297,330 discloses a welded end effector, in which a knot is first tied in the suture, and subsequent fusing the knot to form a stopper. This method is inefficient since it requires the initial formation of a knotted structure, and then the application of energy may result in notches or dents due to the inherently open initial knotted structure. Similarly, U.S. Pat. Nos. 8,323,316 and 8,333,788 each disclose the use of a knotted end effector, where the end effector includes a knot including a plurality of throws. The initial formation of a knotted structure is to be avoided through the present invention.

PCT Publication No. WO 2012/004758 discloses a suture thread that is produced with a stopper on the non-needled end of the fiber. It is proposed that the stopper may be molded or heated and the free end of the suture fiber is inserted into the molten polymer to seal the fiber to the stopper. This method of production requires the addition of the secondary component to the base fiber in a molten condition and the thermal exposure to the molten polymer may result in a loss of strength in the base fiber due to elevated temperature exposure.

While the aforementioned publications have attempted to improve sutures by preparing end effectors, each of the attempts have been either ineffective, inefficient, or pose processing problems. There remains a need to produce a stitch initiation feature that does not require significant secondary processing steps, such as the formation of a knot, or the addition of secondary components, such as addition of molten material, and which results in a strong anchor to hold the suture in place.

SUMMARY

The present invention provides sutures, methods of making sutures, apparatuses for making sutures, and methods of using sutures, the sutures including a termination feature at its distal or trailing end. The invention may provide a suture having a first end and second end and a length therebetween, with a termination feature at the second end, and may include a plurality of retainers formed on the surface of the length of suture. The termination feature includes a coiled portion of a suture that has been subjected to exertion of energy to weld the coil into a stable anchor for the suture.

The suture may be formed by various methods, including one method of forming a suture including the steps of providing a length of suture material, the suture having a first end and second end and a length therebetween, and the suture including a plurality of retainers formed on the surface of the length of suture; winding the second end about a winding pin to form a coil, such that the coil does not become entangled; and subjecting the coiled second end to application of energy, the energy being sufficient to melt at least a portion of the coiled second end and form a solid unitary termination feature.

The method may include a method of continuously forming at least two sutures, each suture having a termination feature at a distal end and formed from a continuous line or strand of suture material. This method may include the steps of: providing a suture fiber having a first end and a second end, and an axial length suitable to form a termination feature-containing suture, the suture fiber being contained in such a fashion that the first end of the suture may be pulled though a winding pin without damage to the suture fiber; inserting the first end of the suture through a first end of a winding pin and out the second end of the winding pin, where the winding pin is disposed within an open interior of a welding die; gripping the first end of the suture with a gripping element, and pulling the first end of the suture in approximately a 90 degree angle with regard to the central axis of the winding pin; causing the suture to be wound about the outside of the winding pin so as to create a coil of suture; moving a welding horn into contact with the coil of suture; applying energy to the coil of suture so as to deform the coil of suture; allowing the deformed coil of suture to solidify to form a termination feature; and may additionally include the step of severing the suture at a location between the termination feature and the second end of the suture.

An apparatus may be included, which is used for forming a suture having a termination feature. The apparatus may include, among other components, a welding horn having a welding tip; a welding die having an open interior sized to be similar to the welding tip; and a winding pin disposed within the open interior of the welding die, the winding pin having a first end and second end and an open axial center connecting the first end and second end. The apparatus may further include a gripping element for grasping the suture material and pulling it to a desired length during the formation process.

There is also provided a method of using a suture including first having a suture, the suture having a suture having a first end and second end and a length therebetween; a termination feature at the second end; and may have a plurality of retainers formed on the surface of the length of suture. The termination feature may include a coiled portion of the suture that has been subjected to exertion of energy to weld the coil into a stable anchor for the suture. The method includes the step of inserting the first end of a suture through bodily tissue and pulling the length of suture through the tissue until the termination feature abuts the tissue.

DETAILED DESCRIPTION

Figure 1:
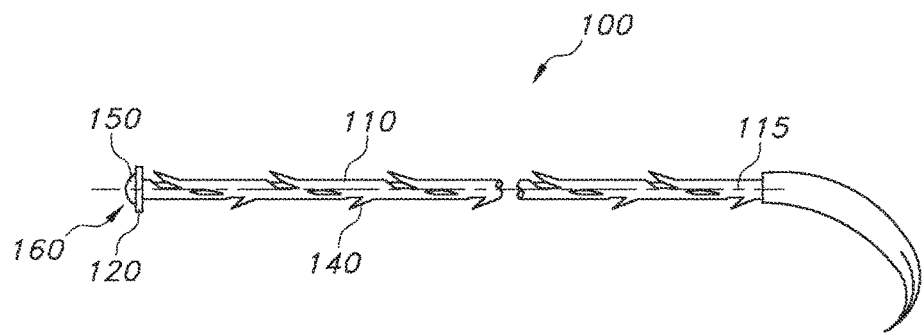
FIG. 1 depicts one exemplary suture of the present invention, which includes a termination feature at its distal end.

The present invention relates to sutures having a suitably strong end effector or termination feature at a non-needle end of the suture device. More particularly, the suture may include at least one retainer along its axial surface and may more desirably include a plurality of retainers. The suture may therefore be known as a self-retaining suture, such as those known and described in U.S. Patent Publication No. 2005/0267531 and U.S. Pat. No. 8,100,940, the entire contents of each of which are incorporated herein by reference. The retainers, if used, may be formed by any desired means, including cutting, shaping, molding, or other retainer-forming means. The description below will reference a suture having retainers formed on its surface, but a suture with no retainers (e.g., an "unbarbed" suture) may be used in the present invention.

The suture device may include multiple strands that are interconnected and therefore may include more than one trailing (or non-insertion, or non-needle end). Any or all of the trailing ends may include a termination feature of the present invention. As used herein, the terms "termination feature", "end effector" and "anchor" may be used interchangeably, and refer to the anchoring device at the trailing end of a suture. The present anchors offer a number of improvements over the prior attempts to prepare an anchoring element, including improved strength, and easier/less costly manufacturing parameters. The present invention forms an anchor without requiring the addition of materials (such as molten materials or other added elements) and also forms the end effector without the initial step of forming a knot prior to welding. The present anchor provides a strong fused termination device at the non-needle end of the suture, which adds stability and strength to the device. Further, the present invention allows for a number of varying shapes depending upon the desired use. The invention requires minimal thermally induced fiber property losses, since the formation need not expose the device to elevated temperature conditions. The present invention is capable of being formed in a continuous in-line processing methodology, which reduces manufacturing costs and allows repeated suture formation with ease.

In one embodiment of the present invention, a method of forming an anchor at a non-needle end of a suture is provided. The suture material includes at least one polymeric fiber, which has a first end, second end, and a body therebetween, where the body extends along a central longitudinal axis. The suture may include any material or combinations of materials that are suitable for use in surgical procedures, including polymeric and/or metallic materials. Further, the material of the suture desirably should include weldable materials, such as those materials that can be melted and/or deformed under the presence of energy, including ultrasonic energy. The suture material may be absorbable or non-absorbable, and may include, for example, polydioxanone, polyglycolic acid (PGA), polylactic acid (PLA), polycaprolactone (PCL), trimethylene carbonate, and copolymers thereof, as well as polypropylene, polyvinylidene fluoride, polyamide (nylon), polyester (polyethylene terephthalate), and other commonly used suture-forming materials.

The resulting suture has a length of suture extending between its first and second ends along its central longitudinal axis, and may have any cross-sectional configuration, including circular, elliptical, triangular, square or diamond-shaped, and the like. The outer surface of the suture body may have one or more retainers formed thereon, such as cut retainers as explained above. The suture may be of substantial length and stored in a spool or other housing which allows for easy removal of the suture strand without entangling the suture. For example, a spool of suture may include sufficient length of suture to form at least five termination feature-containing sutures, or at least ten termination feature-containing sutures, or at least fifty termination feature-containing sutures. The first end of the resulting termination feature-containing suture is the "insertion" or "leading" end, and may include a component to allow for insertion into tissue, such as a needle. The second end is the trailing or distal end. The first end (the insertion end) may be formed by severing a continuous length of suture material either before or after the formation of a termination feature of the present invention, and may include a needle secured thereto. Thus, at least two implantable sutures each including a termination feature (anchor) can be formed from a continuous length of suture formed in accordance with the methods described herein. Alternatively, the termination features may be formed on an individual length of suture, without the need for cutting the suture during the termination feature forming process.

The resulting termination feature-containing suture includes, at its second or trailing end, a termination feature. The termination feature generally includes a wound coil of suture, which has been subjected to energy sufficient to weld the suture coil to itself. The resulting termination feature has improved strength and can be used as an anchor to hold the suture in place after insertion in tissue, where the termination feature abuts the tissue into which the suture is inserted, providing an anchoring effect. One particular embodiment of the termination feature includes a termination feature which is free of any other components added to it, such as adhesives or strengthening agents. This embodiment may thus provide a termination feature that consists of the suture material and no added elements or components. The termination feature may be any shape, and may have an open interior (an "eyelet") or may have a closed structure. As noted above, the termination feature avoids the step of first forming a knotted structure and then subjecting that knotted structure to energy. The desired termination feature is formed into a coil, desirably while within the forming apparatus, and then that coil is subjected to energy to cause sufficient welding. It is understood that avoiding the need for initially forming a knot is not only more efficient but results in an anchor that is structurally different than knotted sutures.

In one method of forming a suture with a termination feature, the polymeric suture fiber is inserted in a cavity which contains a slotted pin element. The fiber is engaged with the slotted pin element within the cavity. Rotation and optional axial movement of the slotted pin element causes the fiber to wind about the circumference of the pin within the cavity forming a spiraled coil of fiber. Once a sufficient length of fiber has been wound into the cavity into a spiraled coil, the resulting coil of fiber is subjected to an energy source, such as ultrasonic forces. The transference of energy is achieved through the contact of a contact unit interface with the coiled material, and the coiled fiber is converted into fused polymer geometry having the general shape of the contact unit interface. The coiled fiber is preferably not entangled, that is, there are not overlapping coils such that the coil cannot be unwound without forming knotted regions. In the present invention, after the coil is formed, if the suture is pulled in either direction, the coil will unwind without knot formation.

The contact unit interface may include a welding horn and/or die. If desired, the suture material may be cut either prior to or after the formation of the end effector. In some methods, any excess suture material is severed prior to welding the termination feature. After the termination feature is formed, the remaining length of suture may be cut at a desired location, providing the length of suture with termination feature on its second end. This end that is left after cutting may be a cut that forms the leading end of the suture, onto which a needle or other insertion device may be secured.

The present invention also includes methods of packaging the inventive sutures, such that the suture and/or end effector does not become tangled or otherwise stuck to the packaging material.

As will be described in greater detail below, one type of an apparatus to form the termination feature of the present invention includes components such as a welding horn and base, the base including a winding pin and welding die. As used herein, the terms "down" or "downward" shall refer to the direction moving from the top of the welding horn toward the base of the winding post. The terms "down" and "downward" can apply to any component in the invention. Similarly, the terms "up" or "upward" shall refer to the direction from the base of the winding post to the top of the welding horn. The terms "up" or "upward" similarly can apply to any component in the invention. For example, if welding horn (200) is located in an "up" position, this means that the welding horn 200 has been moved in a direction that moves away from the winding post and welding die. Likewise, if the welding horn 200 is located in a "down" position, this means that welding horn 200 has been moved in a direction towards the winding post and welding die.

Referring to FIG. 1, one example of a self-retaining suture device 100 is illustrated. The suture device 100 in FIG. 1 includes a monofilament fiber 110, but it is understood that multi-filament sutures, including braided sutures and sutures having concentric filaments may be used. In FIG. 1, the suture 100 has been produced with a triangular cross section, but other cross-sections may be useful, including, for example, a circular cross-section. The monofilament fiber 110 has an outer surface, and may include a plurality of retainer elements 140 that have been cut into or otherwise formed on the outer surface of the fiber 110. Methods of cutting retainers 140 into a suture 100 are well-known, and include methods described in U.S. Pat. No. 6,848,152, the content of which is incorporated by reference herein in its entirety. Retainer elements 140 are not required, and the sutures of the present invention may be free of retainers on the suture.

The suture 100 includes first, leading end 115 (which may be termed the "proximal end" or "insertion end" and may optionally include a needle 130 secured thereto) and second, trailing end 150. The trailing end 150 of the fiber 110 is produced with a termination feature 120 (also referred to as an "end effector" or "anchor"), which is formed by the techniques outlined in this disclosure. The termination feature 120 desirably consists of the suture material itself, but may optionally include additives or strengthening materials before or after welding. In embodiments where the termination feature 120 is free of additives or strengthening materials, it is understood that trace materials of contaminants may be present, but that other materials other than the suture material itself are not intentionally added.

The termination feature 120 may be produced in a variety of geometries, including having a circular, triangular, rectangular (including, for example, diamond or square shaped), or other geometric cross section. Edges and corners of the termination feature 120 may be rounded or smooth, if desired. The termination feature 120 may have any desired thickness, and may have varying degrees of thickness throughout the termination feature 120 if desired. Further, there may be a tapered section extending from the outer surface of the suture fiber 110 to the termination feature 120. Various geometric configurations may be considered depending upon the use of the suture 100, including the location of placement in a patient, the type of tissue to be secured and the necessary strength of the fixation. In soft tissues, for example, where there is the potential for dilation of the suture tract, it may be desired to provide a termination feature 120 with a large bearing surface, oriented perpendicular to the central axis of the fiber 110. The termination feature 120 abuts the tissue into which the suture is inserted, having an anchoring effect.

FIG. 1 shows such a device, having a termination feature 120 that is oriented so as to be perpendicular to the central axis of the fiber 110. That is, the termination feature 120 has a major diameter that is perpendicular to the central axis of the suture fiber 110. The termination feature 120 may have a generally flat disk-like shape or it may have a curved distal end 160, as can be seen in FIG. 1. In firm tissues, it may be desirable to produce a termination feature oriented such that its diameter is substantially parallel to the axis of the fiber 110, such as a "lollipop-type" configuration seen in FIG. 11B. In some instances, it may be desirable to lock the suture back onto itself through the use of a looping mechanism, or with a termination that provides an engagement feature or open eyelet through which a suture may be passed.

The suture 100 may have any desired length and cross sectional diameter, including those described in greater detail below. It is particularly desirable that the cross-sectional diameter of the termination feature 120 be greater than the largest measured diameter of the suture 100. Thus, the ratio of the diameter of the termination feature 120 to the largest diameter of the suture 100 should be greater than 1.1:1, and may be up to about 10:1. More desirably, the ratio of the diameter of the termination feature 120 to the largest diameter of the suture 100 may be about 4:1 to about 8:1. The size and shape of the termination feature 120 will be described in greater detail below, but it is useful to provide a termination feature 120 that is large enough to act as a suitable anchor, while at the same time having a termination feature 120 that is sufficiently small to be manufactured and packaged appropriately. As used herein, the term "diameter" does not necessarily refer to a circular cross-section, and the term "diameter" can refer to the largest distance from opposing ends of device, such as opposing corners of a square.

The termination feature 120 is desirably composed of the suture fiber 110, which has been wound and subsequently formed into a solid structure, such as through the application of energy. As noted, it is particularly preferred that the termination feature 120 be free of any additional materials, however, it may be desired to include one or more compositions that are capable of filling in any potential gaps in the wound fiber and/or strengthen the final welded termination feature 120. As will be described below, the fiber 110 is wound into a coil while the suture is contained in the welding apparatus, and is then welded to form the termination feature 120. In this method, there is no pre-forming step, such as the formation of a knot or other structure, prior to winding and welding. The wound portion of the fiber 110 may include a plurality of retainers 140 or it may be free of retainers 140.

Figure 2:
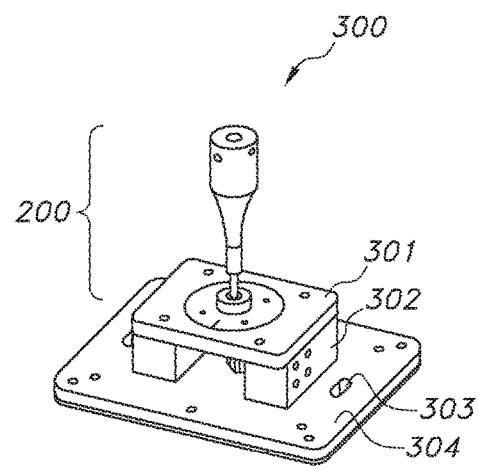
FIG. 2 depicts one embodiment of an assembled welding horn and welding nest.
Figure 3:
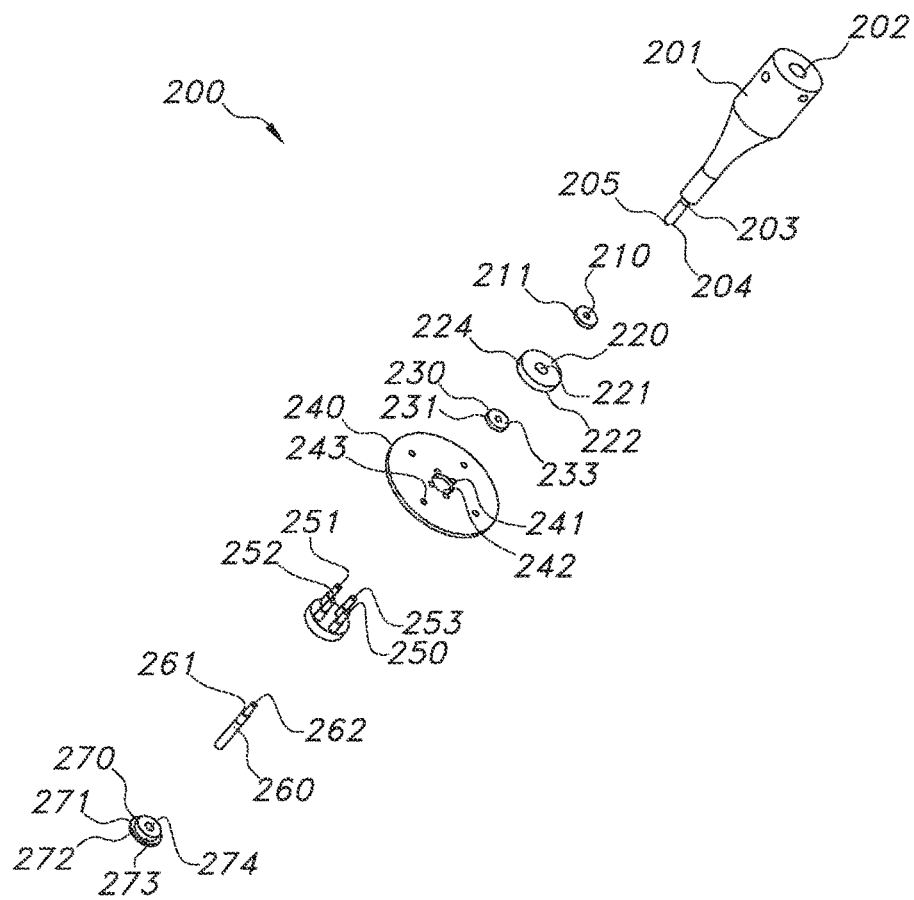
FIG. 3 depicts an exploded view of the components of a welding horn, which may be useful in the present invention.

Referring to FIGS. 2 and 3, an apparatus for manufacture of the suture 100 and termination feature 120 is depicted. The apparatus may include a welding horn 200 and a welding nest 300 (welding nest 300 may be considered the "base" of the welding apparatus). The welding horn 200 is designed to mate with the welding nest 300 to provide the termination feature 120 as desired. The welding nest 300 may include a raised mounting plate 301 that is mounted to a top side of support pillars 302. In the depicted Figure, two pillars 302 are shown, but more than two support pillars 302 may be used if desired. Each pillar 302 has an upper end and bottom end, the upper end being secured to the mounting plate 301. The bottom end of the pillar 302 is mounted to a nest base plate 304. The pillars 302 may be detachable from either the mounting plate 301 or the nest base plate 304. The nest base plate 304 may include a means to attach the welding nest 300 to a secure surface for welding. For example, the nest base plate 304 may include a series of through bore mounting holes 303 that enable attachment of the welding nest 300 to a supporting structure during use.

Referring to FIG. 3, a number of components in the welding assembly are depicted. This Figure includes a number of individual components that are described herein in detail, but it is understood that modifications of assembly may alter or remove one or more of the components described herein without modifying the function and use of the assembly. The assembly seen in FIG. 3 includes an ultrasonic horn 201, which is a length and design that is suitable to the frequency of the particular ultrasonic generator that has been selected. Frequencies of from about 20 kHz to about 40 kHz, and more specifically about 30 kHz may be useful in forming the termination feature 120 of the present invention, and the ultrasonic horn 201 of the invention should be suitable to deliver the intended frequencies. The ultrasonic horn 201 may be produced with a threaded bore 202 at its upper end that is utilized to attach the horn to an ultrasonic welding booster/transducer assembly (not shown). The horn 201 has an axis that runs through its length from the threaded bore 202 to an ultrasonic horn tip 205.

The horn 201 may be any desired shape or configuration, including a cylindrical shape, or having a cross-section that has varying geometry. Preferably, the horn 201 is tapered, having a larger cross-sectional diameter at its upper end and tapering to a smaller cross-sectional diameter at its lower end. The horn 201 may include a stepped elliptically shaped cylindrical wall 203. In a preferred embodiment, the ultrasonic horn 201 is produced with a reduced diameter shoulder 204 that is intended to engage with an insert ring 210 during the welding process. The insert ring 210 is desirably polymeric material, but may be metallic or include other materials if desired. An ultrasonic horn tip 205 is disposed at the lower end of the horn 201. The ultrasonic horn tip 205 is sized and shaped to fit within a receiving bore 222 of a welding die 220. The horn tip 205 and the welding die 220 are sized and shaped so as to provide the desired structure and geometry of the termination feature 120. In use, the coiled suture fiber is placed between and within the horn tip 205 and welding die 220, and then energy is applied.

Figure 24:
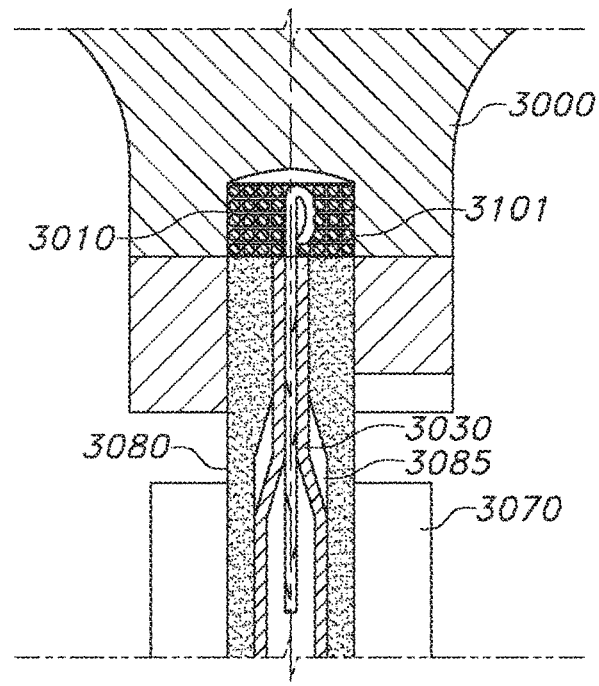
FIG. 24 shows the welding assembly of FIG. 22 as a suture is coiled.
Figure 25:
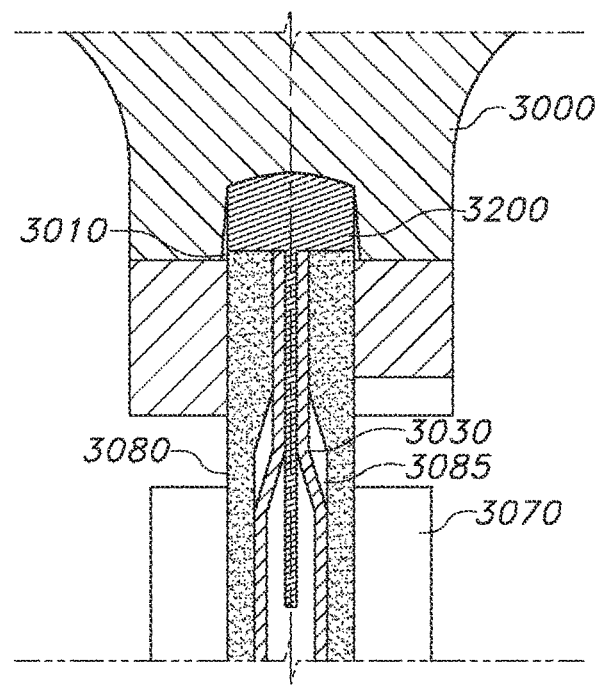
FIG. 25 shows the welding assembly of FIG. 22 as a termination feature is formed.
Figure 26:
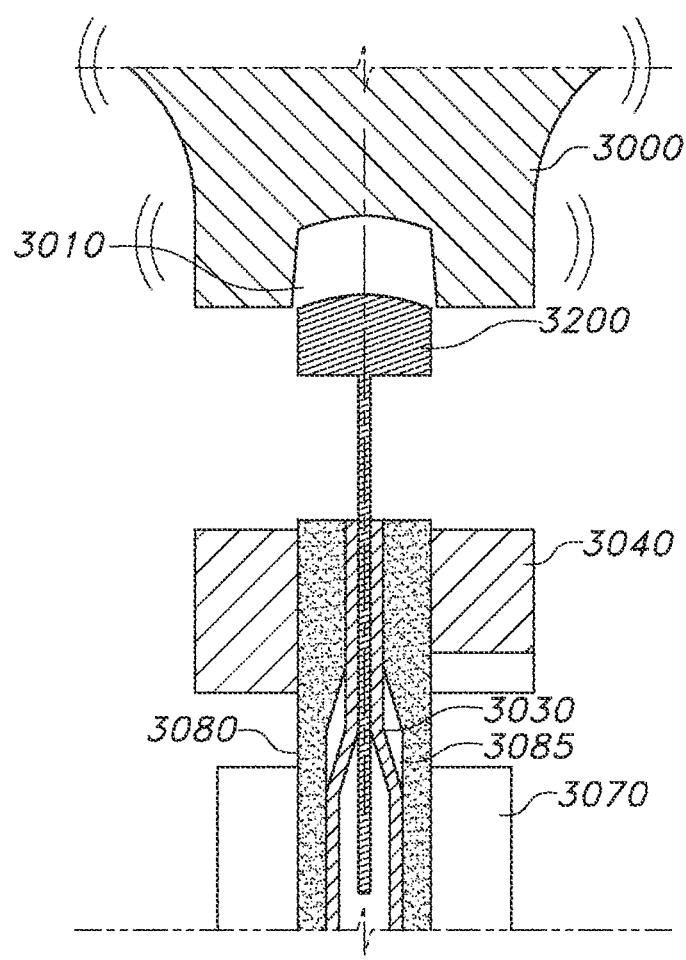
FIG. 26 shows the release of a termination feature from the assembly of FIG. 22.

It may be desired to include an elastic element in contact with the welding die 220, such as beneath the welding die 220, so as to allow the welding die 220 to remain engaged with the horn tip 205 during the application of energy. As the horn 201 oscillates vertically, the spring force acting upon the die helps to maintain the welding die 220 in contact during the weld cycle. It has also been found that if the welding die 220 remains in substantially tight engagement with the horn 201 during the cycle, that the welding of the upper coils of fiber may be diminished and the weld that is produced is similar in appearance to those produced within a cavity in the face of the horn 3000 as illustrated in FIG. 24. Preferred welding conditions are achieved through the addition of a frictional drag component to the cage leg elements. The necessary frictional drag component of die movement ensures that the welding die 220 does not vibrate in unison with or in exact frequency with the ultrasonic horn 201. While the elastic element and drag elements may be achieved through the use of elastic material and ball plungers, the use of springs, air or other springs, as well as spiral displacement of the welding die 220 or the use of external damping elements such as brake or shock absorber style elements are also feasible.

The welding die 220 is placed in a location that may secure the suture fiber 110 between it and the horn tip 205 in use. Thus, the welding die 220 may be disposed in a coaxial configuration with the horn 201, such that if the horn 201 and/or the welding die 220 are moved in an axial fashion (e.g., up and down), a suture fiber 110 may be placed into the space therebetween.

Figure 4:
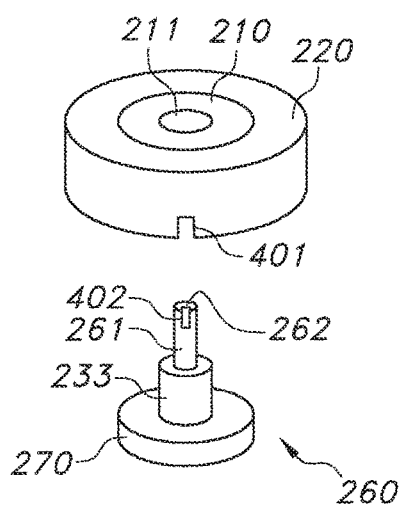
FIG. 4 depicts a welding die and winding pin assembly in separated configuration.

The welding die 220 may include a receiving bore 222 that is sized and shaped to match the desired edge shapes and sizes that are desired for the final termination feature 120 to be formed. The external size and shape of the ultrasonic horn tip 205 is sized and shaped to mate with the receiving bore 222 so as to form the final termination feature 120. Additionally, the welding die may include a central counter bore 224 that is sized to receive insert ring 210. As can best be seen in FIG. 4, the outer diameter of the insert ring 210 is sized to fit tightly into the central counter bore 224 of the welding die 220. The insert ring 210 and/or the welding die 220 may include a feature or series of features on its underside (not seen in FIG. 4), which will engage with posts 252 of guide unit 250 for secure attachment. For example, the welding die 220 may include a plurality of through bores 221 as seen in FIG. 3. FIG. 4 shows the relationship between welding die 220 and winding pin 260. As can be understood, the shapes and sizes of the die and horn components will dictate the resulting shape and size of the termination feature 120.

The various components described above may be made from any desired materials, provided that the materials selected are suitable for withstanding ultrasonic frequencies and delivering to the suture 100 to provide the termination feature 120. For example, the insert ring 210 may be manufactured of any suitable polymer material including polyolefins, polyesters, pvdf, Teflon based materials, PEEK and other suitable polymers. Alternatively, the insert ring 210 may be made from metallic materials with a lower hardness than the material utilized to produce the ultrasonic horn 201, such as bronze, aluminum, and other metallic materials having a lower hardness than the ultrasonic horn 201. The ultrasonic horn 201 may be made from metallic materials, such as titanium, aluminum, or stainless steel.

The welding nest assembly 300 includes a fixture plate 240, which is placed and held within the mounting plate 301, and may be removable or may be secured in the mounting plate 301. The fixture plate 240 may include a central counter bore 241. The welding nest 300 may also include a post insert plate 230. The outer diameter of the post insert plate 230 is sized and shaped to fit snugly within the counter bore 241 located within the fixture plate 240. The post insert plate 230 may be removably or permanently secured to the fixture plate 240 and may include a series of through bores 243 to receive posts 252 of guide unit 250. The post insert plate 230 may additionally incorporate a central through bore 233. The central through bore 233 is sized to slidably receive a winding pin 260.

The fixture plate 240 may be produced with a means to secure the fixture plate 240 to the mounting plate 301. For example, as can be seen in FIG. 3, fixture plate 240 includes several through threaded bore features 243 that are located about the perimeter of the plate 240. These threaded through bores 243 are utilized to attach the fixture plate 240 to the mounting plate 301. The central portion of the fixture plate 240 may be produced with a through bore 242 for passage of the winding pin 260.

The assembly may optionally include a guide unit 250, which may include a through bore 251 that is slidably engageable with the winding pin 260. Extending from the upper surface of the guide unit 250 are a plurality of posts 252 that may have a shouldered or larger diameter region 253. The posts 252 are arranged and sized to mate with through bore holes 243 in the fixture plate 240. In some embodiments, there may be four posts 252, but any desired number of posts may be included. The shouldered or larger diameter region 253 of post 252 is desirably larger in diameter than the through bore holes 243 in the fixture plate 240 to provide a secure hold. The winding pin 260 may have a tapered inner through bore 262. Further, the winding pin 260 has a first end 263 and a second end 261, the first end 263 having a larger outer diameter than the second end 261, and the first end 263 optionally being coupled with a winding knob 270. The second end 261 of winding pin 260 may be slidably engaged with the central opening of the post insert plate 230.

FIGS. 4-10 show examples of a useful welding die, post insert, and winding pin, as well as depict one method of the formation of a termination structure 120 of the present invention. FIG. 4 illustrates a welding die assembly 220 in an "up" position relative to the welding post 233 and the winding pin 260. The winding pin 260 may have a hollow tapered bore 262 that exits at the second end 261 of the pin. The hollow interior of the winding pin 260 is desirably sized to have a larger diameter than the diameter of a suture fiber 110 to be used. The suture fiber 110, prior to formation of a termination feature, can therefore be fed through the interior of the winding pin 260 without restriction or damage. The internal diameter of the pin 260 may be tapered, ending at a notch 402 at the second end 261 of the pin 260. The interior diameter of the pin 260 may be smaller at the second end 261 of the pin 260 than on the first end 263 of the pin. This inner taper may be useful in enabling smooth feeding of a suture fiber into the pin 260. Welding die 220 may have a partial channel or notch 401 on its downward side, with the channel 401 being sized sufficiently to allow passage of a suture fiber 110 therethrough.

Figure 5:
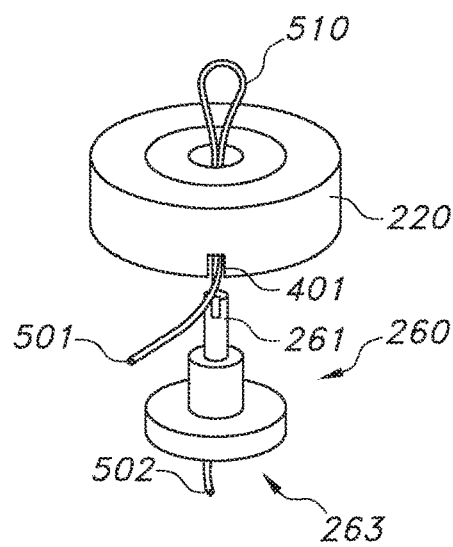
FIG. 5 depicts one step in feeding a suture into the welding die assembly.

Referring now to FIG. 5, one method of feeding a length of suture into the winding pin is depicted. In this embodiment, a length of suture 510 may be inserted through the first end 263 of the winding pin 260 and fed "upward" towards the second end 261 of the winding pin 260. Since there is no pre-formed knot or other structure, the suture 510 is capable of being fed through winding pin 260 and out second end 261. The suture 510 may then be bent as illustrated, and the first end 501 of the suture 510 may be passed through the channel 401 and through the notch 402. Second end 502 of the suture 510 remains sticking out through the first end 263 of the winding pin 260. Although the die 220 is illustrated in a separated condition from the winding knob 270, the die 220 may be located in a nested position on top of the winding knob 270.

Figure 6:
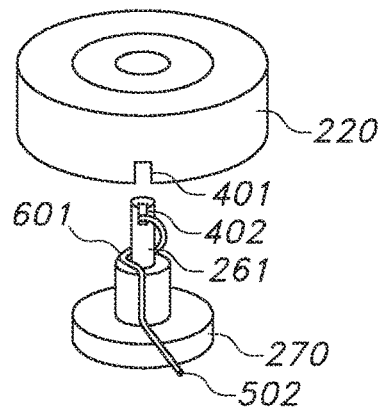
FIG. 6 depicts another step in feeding a suture into the welding die assembly.
Figure 7:
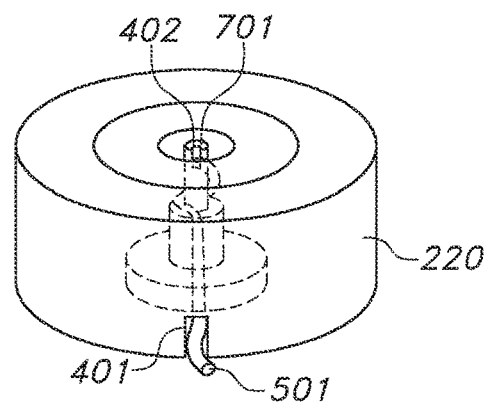
FIG. 7 depicts the suture fed into the welding die assembly.

Referring now to FIGS. 6 and 7, the rotation of the winding pin 260 is illustrated. It should be noted that the welding die 220 is illustrated in the "raised" position only for the sake of providing visualization of the suture fiber 510 as it would form a wrapped geometry 601 when inside of the welding die 220. In use, the welding die 220 may be lowered (or, alternatively, the winding pin 260 raised) so that the winding pin 260 is located within the interior of the welding die 220. FIG. 7 illustrates the position of the winding pin 260 relative to the top of the welding die 220 during winding, with the welding die 220 in the "down" position for the winding operation to be conducted. The winding pin 260 is disposed within the interior of the welding die 220, such that the second end 261 of the winding pin 260 is nearly flush with the upper region of the welding die 220 during the winding operation. This flush configuration and the location of the winding pin 260 in this configuration is identified as reference numeral 701. The suture fiber 510 wrapping is illustrated as a dashed line within the welding die 220. In this configuration, the winding pin 260 and welding die 220 are in the "winding position". As can be seen, the first end 501 of the suture fiber 510 extends out through the channel 401 and notch 402. Although not seen in FIG. 7, the second end 502 of the suture extends through the bottom of the winding pin 260.

Figure 8:
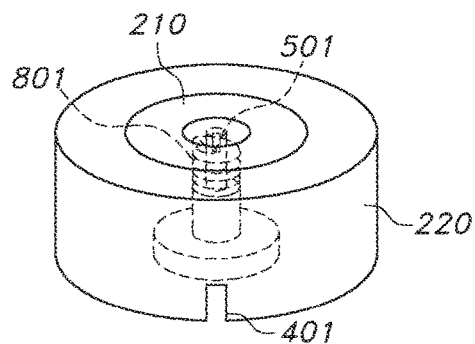
FIG. 8 depicts the suture in wound fashion in the welding die assembly.

Referring now to FIG. 8, the first end 501 of the suture fiber 510 has been wound in the welding die 220 and is illustrated as coil 801 wrapped around the winding pin 260. Alternatively, the first end 501 maybe left partially inside of the channel in the welding die 220 and may be trimmed from the coil 801 either before application of energy to the coil 801, during the down stroke of the ultrasonic horn 201, or after welding is complete. Similarly, the second end 502 of the suture may be cut at any desired time in the welding process or it may remain unsevered until the welding is complete. The length of suture 510 desired is achieved by cutting the second end 502 at a desired length away from the termination feature 120. More desirably, the second end 502 is cut after welding is complete, thus forming a resulting suture having a termination feature.

Figure 9A:
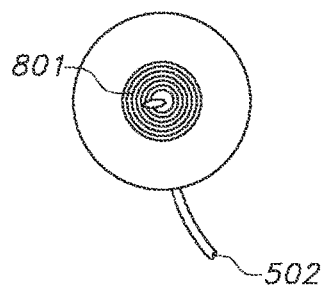
FIGS. 9 and 9A depict the suture in wound fashion with welding die separated from winding pin.
Figure 9:
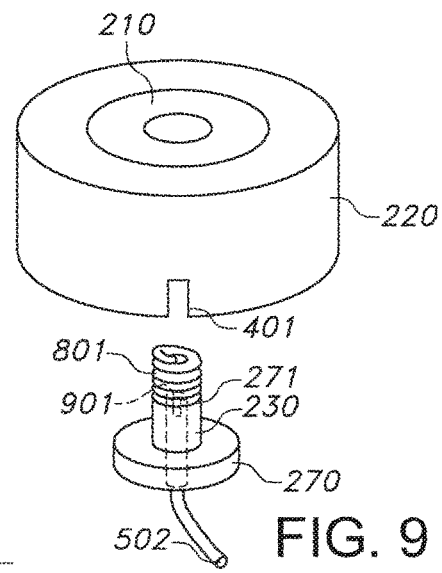

Referring now to FIG. 9, the coiled fiber 801 is illustrated, after winding is complete. The welding die 220 has been lifted in the Figure to allow viewing of the coil 801 only, but it is noted that in use, the welding die 220 would not be removed during use as the interior of the welding die 220 helps to maintain the coil 801 in its coiled configuration. As seen in FIG. 9, the winding pin 260 has been lowered to a "welding position" (identified by reference numeral 901) by retracting the winding pin 260 in the "downward" direction. The winding pin 260 is lowered a sufficient length, such as until the notched end 402 of the winding pin 260 is substantially flush with the top surface of the post insert plate 230. In an alternative embodiment, the winding pin 260 may remain at least partially in an "up" position relative to the post insert plate 230. This alternative arrangement may be useful, for example, in creating an open eyelet structure within the termination feature.

Figure 10:
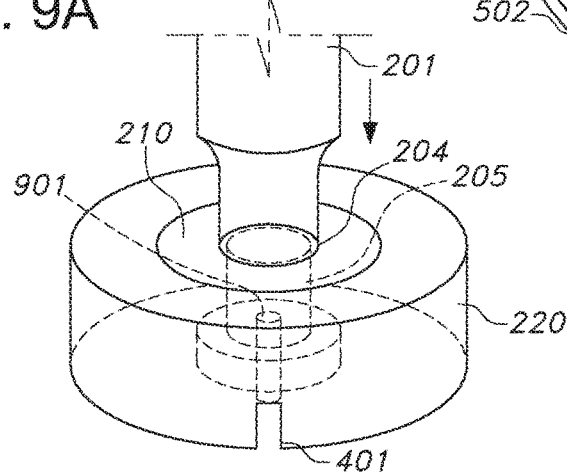
FIG. 10 depicts a welding horn in the downward, welding position.

Referring now to FIG. 10, the ultrasonic horn 201 is lowered into the welding position and is subsequently energized. The operation illustrated in this figure involves the downward motion of the welding die 220 due to contact with the shoulder 204 of the horn 201 with the insert ring 210 during the welding cycle. Therefore, the welding die 220 may be movable relative to the welding post 270. This mode of action enables the adjustment of a gap between the ultrasonic horn tip 205 and the top of the post insert plate 230. The ultrasonic horn tip 205 may be at least substantially, and desirably fully within the open interior of the welding die 220, however, the wall of the tip cylinder 205 does not necessarily contact the inner bore 211 of the insert ring 210. In preferred embodiments, a clearance of about 0.0005-0.002 inches between the side wall of the horn tip 205 and the interior wall of the insert ring 210 is desired to prevent contact.

Thus, in the aforementioned embodiment of the method of formation of a termination structure 120, an assembly including a welding die assembly 220, winding pin 260 extending therethrough and axially movable through the welding die assembly 220, and welding horn 201 are provided. In this embodiment, the welding horn 201 and welding die assembly 220 are moved so as to be separated from each other, and winding pin 260 is contained within the middle open space of the welding die assembly 220. A suture fiber 510 is fed through the inner open interior of the winding pin 260 such that the suture fiber 510 extends out of the second end 261 of the winding pin 260. The winding pin 260 is rotated axially and/or the suture fiber 510 is moved circumferentially about the outside of the winding pin 260 to create a coil 801. A winding knob 270 may optionally be used to effectuate winding.

After the coil 801 is formed, the winding pin 260 may be axially moved in a downward position (e.g., moved in a direction away from the welding horn 201) or it may remain in the "up" position. The welding horn 201 and welding die assembly 220 are brought closer together, such that the coil 801 is entrapped within the space provided by the welding horn 201 and welding die assembly 220. Excess suture fiber 510 may be trimmed from the coil 801 either before application of energy to the coil 801, during the down stroke of the ultrasonic horn 201, or after welding is complete. Energy is applied to the coil 801 and optionally pressure and/or temperature increases may be applied to the coil 801 as well. The suture fiber 510 is allowed to at least partially melt and then the energy (and optional pressure and temperature) are removed, and the now-welded coil 801 is allowed to solidify. The resulting suture 510 now has a suitable termination feature 120 on its end. The suture fiber 510 may be severed at any desired location to provide a desired length of suture.

The welding end of the ultrasonic horn tip 205 is designed to have any of a number of geometries, including flat, conical, spherical convex, spherical concave and polyhedral geometries. It may alternatively have a textured configuration. It has been found that the use of a spherical concave tip design provides lateral compaction of the coiled fiber 801 during the welding cycle. The coiled fiber orientation, coupled with the lateral compaction, provides the transmission of the ultrasonic energy through the tangential contact edges of the coiled fiber 801 to form an essentially solid end termination for the suture 510. In contrast to previous methods in which a knot is first tied in the suture material, this mode of welding restricts the creation of crossing fibers or of a random orientation of fibers, which can create undesirable notch effects in the termination feature. The inventive methods thereby increase tensile strength of the resulting termination feature 120 and provide a structurally different termination feature 120. In addition, the present methods avoid the need for pre-welding steps such as tying a knot, which not only avoids the risk of malfunction, but also allows for easier and quicker processing of sutures.

Figure 11A:
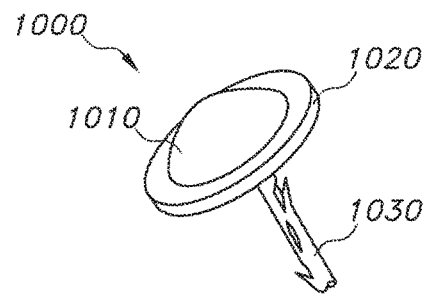
FIGS. 11A-11D depict various termination features.

As noted above, the termination feature 120 may be produced in multiple geometries, depending upon the purpose and desired look and feel. The size and shape of the termination feature 120, as well as any surface texture or configuration, may vary depending upon the desired suture. Various termination feature configurations are depicted in FIGS. 11A-11D. FIG. 11A shows a termination feature 1000 having a large tissue bearing surface. The termination feature 1000 includes a raised surface 1010, such as a bulbous or convex surface, and includes a round circumference 1020. The embodiment of FIG. 11A has an orientation that is perpendicular to the longitudinal axis of the suture 1030. The suture 1030 extends substantially from the center of the termination feature 1000. FIG. 11A may be modified such that the suture 1030 extends from a side of the circumference 1020, giving a "lollipop" type configuration. The thickness and the cross-sectional diameter of the circumference 1020 of the termination feature 1000 may vary as desired.

Figure 11B:
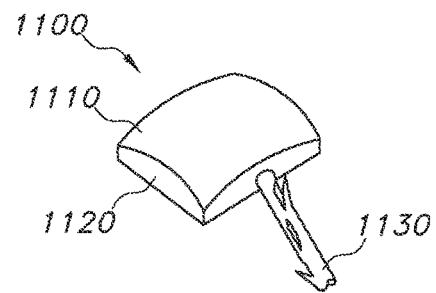

FIG. 11B shows an alternate configuration with a raised surface 1110, but the termination feature 1100 has a square or rectangular circumference 1120. The corners of the circumference 1120 may be rounded or they may have sharp angles. The suture 1130 in this embodiment extends from the outer circumference 1120 of the termination feature 1100, similar to a "lollipop" configuration. FIG. 11B may be modified such that the suture 1130 extends from the center of the termination feature 1100. The thickness and the cross-sectional diagonal of the circumference 1120 of the termination feature 1100 may vary as desired.

Figure 11C:
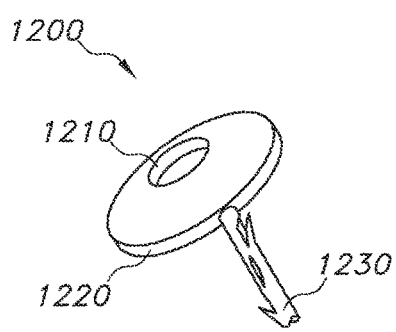
Figure 11D:
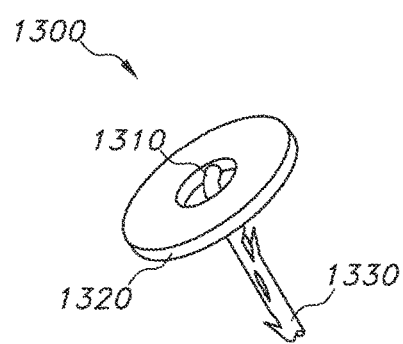

Alternatively, the termination feature may include an eyelet or open configuration, such as that seen in FIGS. 11C and 11D. FIG. 11C shows a termination feature 1200 having a central eyelet 1210, and a rounded circumference 1220. It is understood that the circumference 1210 need not be rounded and may have other geometries. In this configuration, the suture 1230 extends from the side of the circumference 1220, such as a lollipop configuration. The size of the eyelet 1210 may vary as desired, but it is desirable that the diameter of the eyelet 1210 be larger than the cross-sectional diameter of the suture 1230. The interior sides of the eyelet 1210 may be substantially smooth and may be rounded if desired. The eyelet 1210 need not be round and may alternatively be different geometric shapes. FIG. 11D shows a similar termination feature as in FIG. 11C, but the termination feature 1300 of FIG. 11D includes an eyelet 1310, where the suture 1330 extends from the interior of the eyelet 1310. The termination feature 1300 also includes an outer circumference 1320. As with the other termination features, the termination feature 1300 need not necessarily have a rounded circumference, and the eyelet 1310 need not have a round configuration. The size of the eyelet 1310 may vary as desired, but it is desirable that the diameter of the eyelet 1310 be larger than the cross-sectional diameter of the suture 1330.

The termination feature (1200, 1300) may be produced with eyelet features 1220 or 1320 through modifications to the welding process as described previously. For example, the production of a termination feature (1200, 1300) with an eyelet (1220, 1320) may be formed by leaving the winding pin 260 in an at least partially "upward" position during welding, that is, the winding pin 260 may remain at least partially within the interior of the welding die 220 during the welding process (during the application of energy). The winding pin 260 therefore creates a region within the coil during welding. After welding, the pin 260 may be lowered and reveal the anchor including an open eyelet.

The various configurations for termination features, including shapes, sizes, cross-sectional diameters, presence of thicker or thinner regions, or textured surfaces may be produced through the use of a welding die 220 and ultrasonic horn tip 205 that includes the desired shapes, sizes, textures. Alternatively, the termination features (e.g., 120) may be subjected to secondary processing such as stamping, cutting, reforming, annealing, surface treating, abrading, or other mechanical or chemical treatments to produce different geometries, shapes, textures or other characteristics desired. In some embodiments, after the suture is formed with termination feature 120, the suture and/or termination feature may be subjected to a heat sterilization treatment, which may provide some annealing to the suture and/or termination feature 120. Such heat treatment may be at temperatures of from about 40° C. to about 80° C., and more specifically from about 50° C. to about 60° C., and most desirably about 55° C.

Figure 12:
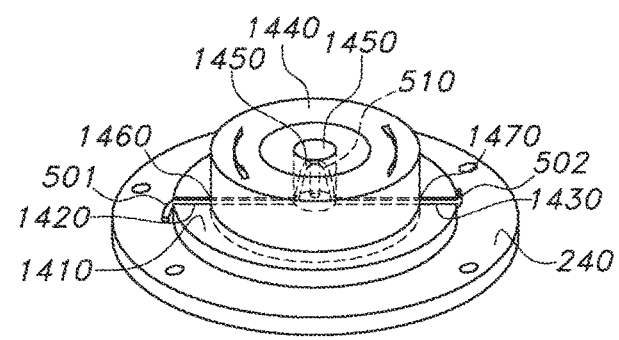
FIG. 12 depicts an alternate method of rotating a suture to form a termination feature.

Referring now to FIG. 12, an alternative method of producing termination feature 120 is illustrated. FIG. 12 includes a suture fiber 510 having first end 501 and second end 502. A welding nest 240 as described above may be used, with a receiving boss 1410 disposed thereon. The receiving boss 1410 includes a first channel 1420 and second channel 1430 on its upper surface, with a removable welding ring 1440 disposed thereon. In this embodiment, the body of fiber 510 extends across the face of the receiving boss 1410 with the first end 501 and second end 502 are disposed on opposing sides of the receiving boss 1410. Thus, the suture fiber 510 lies within a first channel 1420 and second channel 1430, wherein each channel (1420, 1430) is disposed on opposing ends of the receiving boss 1410, allowing the suture fiber 510 to span the welding area in the center of the welding ring 1440. Welding ring 1440 includes a hollow center portion 1450 and opposed notches 1460, 1470, through which the suture 510 may travel. The notches 1460, 1470 are configured to align with first and second channels 1420, 1430. The welding ring 1440 is capable of rotating about the welding nest 240, thereby rotating the suture 510 about a winding pin 1401.

In this embodiment, the welding ring 1440 is rotated sufficiently to cause winding of each of the first end 501 and second end 502 about central winding pin 1401. A channel may be provided in the welding nest 240, which may help guide the rotation of welding ring 1440. Alternatively, the winding pin 1401 itself may be rotated, causing rotation of the suture 510 about the pin 1401. When the suture 510 is sufficiently wound, a welding horn (e.g., 201) is lowered into contact with the center portion 1450, and welding is achieved.

Figure 13:
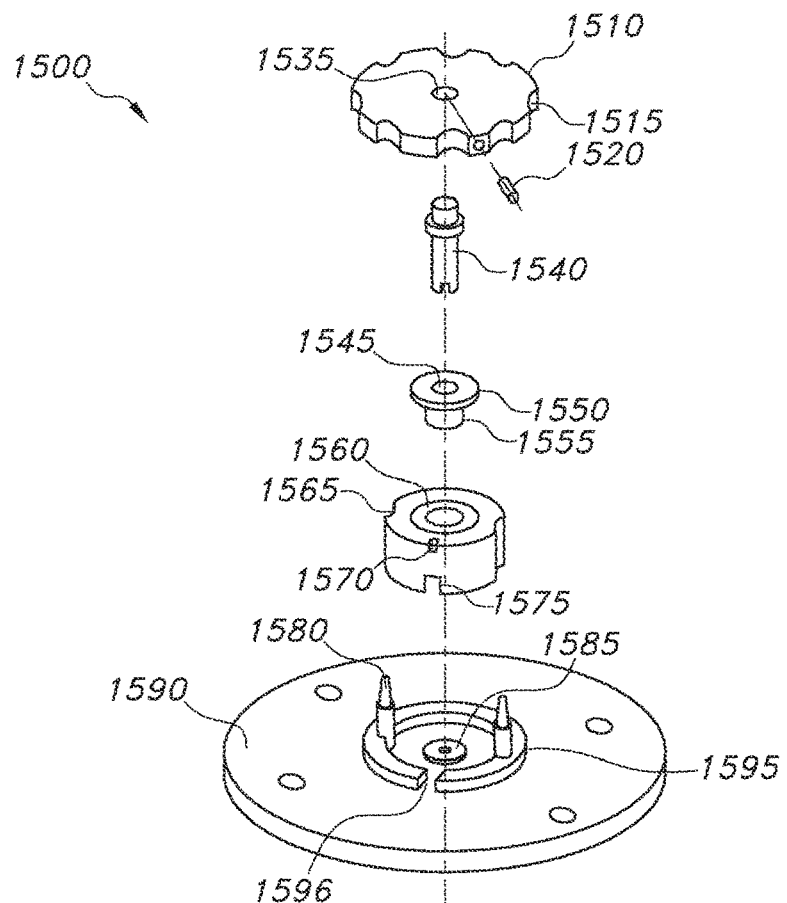
FIG. 13 depicts yet another apparatus and method suitable to rotate a suture and form a termination feature of the present invention.
Figure 14:
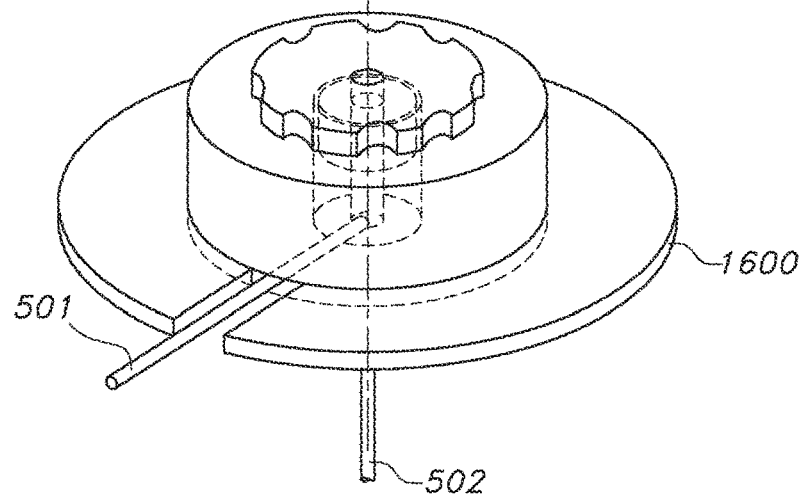
FIG. 14 depicts an assembled view of the components of FIG. 13.

Referring to FIG. 13, an alternate method of producing a termination feature (e.g., 120) is illustrated. A winding nest assembly is utilized that uses a winding pin 1540 that does not remain within the welding die 1570 or welding post during the welding cycle. A fixture base 1590 is mounted to a mounting plate (e.g. 301). Two alignment pins 1580 are fixedly mounted to the fixture base 1590. A boss ring 1595 is incorporated into the fixture base 1590 and is produced with a slotted feature 1596. Additionally, a cavity base post 1585 may be incorporated into the fixture base 1590. The cavity base post 1585 is produced with a tapered through bore that extends through the fixture base 1590. The welding die 1570 is produced with alignment slots 1565 that engage with the alignment pins 1580 mounted in the fixture base 1590 during the welding cycle. Alignment pins 1580 may be tapered to provide a better fit. The welding die 1570 also incorporates an insert ring 1565 with a through bore that is shaped and sized to fit around the tip of the ultrasonic horn (e.g., 201) during the welding cycle without contacting the ultrasonic horn 201. An optional stripper guide 1555 may be utilized during the winding portion of the production method. The stripper guide 1555 is held in the "down" position within the welding die 1570 while the winding pin 1540 is rotated. Winding pin 1540 includes a notch 1545 on its "down" side (e.g., the end of the pin 1540 furthest away from welding horn). The stripper guide 1555 has a flanged edge 1550 that is graspable by the operator during winding. The stripper guide 1555 also has a through bore that is sized to receive the winding pin 1540 during fiber winding and is larger in diameter than the winding pin 1540. The winding pin 1540 is secured to a winder knob 1510 with the stem 1525 of the winding pin 1540 inserted into a receiving bore 1535 of winder knob 1510, and may be fastened via any desired means, such as with a set screw 1520.

In use, the first end 501 of the fiber 510 is passed through the cavity base post 1585 from the bottom side 1600 of the fixture base 1590. The fiber 510 is laid into the slot 1596 into the boss ring 1595, and the welding die 1570 is lowered into position between the alignment pins 1580. Once the welding die 1570 is in position, the stripper guide 1555 and the winding pin 1540 are inserted into the top of the welding fixture. The fiber 510 is engaged with the notch 1545 in the winding pin 1540 and the notched end of the winding pin 1540 is in close approximation to the cavity base post 1585. The winding pin 1540 is rotated and the free end 501 of the fiber 510 is coiled about the winding pin 1540, as previously described. Once the fiber coil (e.g., 801) is complete, the winder knob 1510 and pin 1545 may be removed from the die 1570 along with the stripper guide 1555. An ultrasonic horn (e.g., 201) is lowered into position as previously described and energy is applied to the coil. Once sufficient energy has been applied to the suture, and the welding of the termination feature is complete, the formed termination feature 120 may be removed from the die 1570 along with the remaining length of fiber 510.

Referring now to FIGS. 15 through 21 a sequence of operation for an automated version of the termination feature formation is described. This method is useful in that it enables substantially continuous production of sutures having a termination feature, the continuous production using one continuous spooled (or otherwise stored) length of fiber to create a plurality of sutures. In this embodiment, a substantial length of suture, which may have a plurality of retainers on its outer surface, is first prepared and contained in such a fashion that the suture material can be pulled without snagging or entanglement. For example, it may be desired that the suture be contained on a spool, which may be unwound by pulling on a first end of the suture. The amount of suture in the spool may vary, but it is desired that there be sufficient spooled suture to form at least two sutures having termination features, and more desirably at least five sutures having termination features, and more desirably at least ten sutures having termination features. As the formation of termination feature-containing sutures progresses, less suture material will inherently be contained within the spool. The process may also be utilized with stranded material in a semi or a fully automated production.

Although the method described herein refers to a continuous spool or housed length of suture material, the method may be useful with separate, discrete suture strands that have been cut to a desired length. In this method, the second end of the suture is pre-cut, as opposed to being a continuous length of suture that is contained in a spool or other housing.

Figure 15:
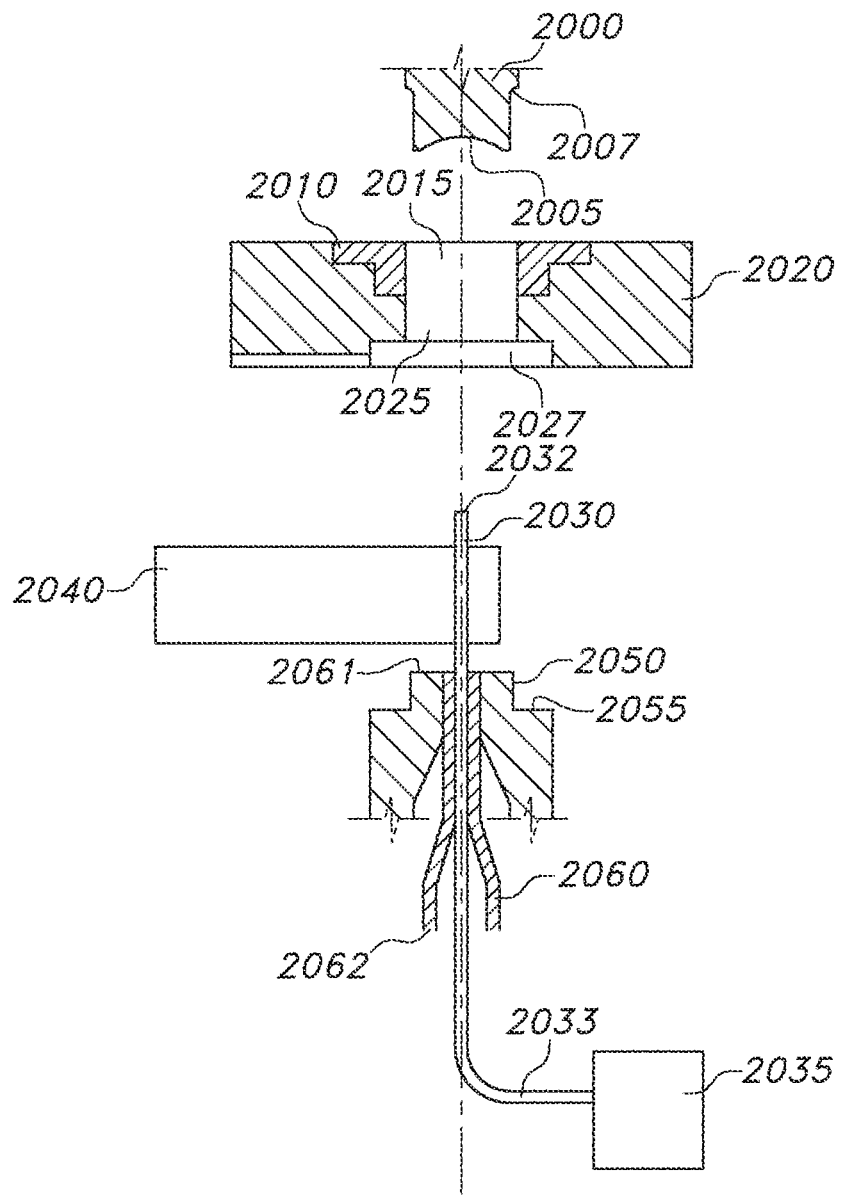
FIG. 15 depicts one step of a method of continuous processing of termination feature-containing sutures.

FIG. 15 depicts several components useful in this method and the assembly for use in the method. As described above, the term "up" or "upward" or "upper" refers to the direction from the winding pin towards the horn. As also previously described, the terms "down", "downward" or "lower" refer to the direction from the horn towards the winding pin. Starting at the most "upward" component in FIG. 15, and traveling "downward", the components in FIG. 15 include a horn 2000 (sometimes referred to as an "ultrasonic horn", but it is understood that other energy aside from ultrasonic energy may be used), an insert 2010, a die 2020, a gripping element 2040, a cavity base 2050, and a winding pin 2060.

The horn 2000 includes a tip 2005, which may be concave or may include other geometry or surface features or textures. The horn tip 2005 is sized and shaped to snugly fit within the open central region 2015 of insert 2010. There may be a slight gap between the horn tip 2005 and the central region 2015 of the insert 2010, if desired. The insert 2010 is itself designed and configured to fit snugly and securely in the open central region 2025 of die 2020. The insert 2010 and die 2020 both have an open central region in their axial centers (2015, 2025), forming an open central region in the assembly, to allow the passage of components such as the winding pin 2060 and suture 2030, and to allow entry of the horn 2000 into the open centers (2015, 2025). The open central regions (2015, 2025) may be sized so as to allow a suture having retainers to be fed into and through the central regions (2015, 2025) in a first direction, such that the first part of the suture (e.g., the insertion end) is fed through the central regions (2015, 2025) first.

The cavity base 2050 has an open central axial interior, into which a winding pin 2060 may be at least partially inserted. The winding pin 2060 similarly has an open central interior extending along its longitudinal axis, starting at first end 2061 and ending at second end 2062. The first end 2061 of the winding pin 2060 is located at the upper region of the winding pin 2060, while the second end 2062 is located at the downward region of the winding pin 2060. The first end 2061 may have a notch or channel 2065 at the circumference of the winding pin 2060, extending into the open central interior, the notch 2065 being sized and shaped to accommodate the suture 2030 therein.

The suture 2030 extends through the open axial center of the winding pin 2060, where a first end 2032 of the suture is on the upper side of the winding pin 2060, and the second end 2033 of the suture 2030 is on the downward side of the winding pin 2060. If the suture 2030 is a self-retaining suture including a plurality of retainers or barbs, the free end of the barbs face towards the first end 2061 of the winding pin 2060 (e.g., in the direction of the welding horn 2000). The internal diameter of the pin may be tapered, ending at a notch at the second end of the pin. The interior diameter of the pin may be smaller at the second end of the pin than on the first end of the pin 2060. This inner taper may be useful in enabling smooth feeding of a suture fiber into the pin. In this configuration, the suture 2030 can be freely pulled towards and through the first end 2061 of the winding pin 2060 without damage to the retainers. The first end 2032 of the suture 2030 may be gripped by a gripping element 2040. Gripping element 2040 is any desired component that can suitably hold the suture and maintain its grip through processing, and should be suitable to hold the suture 2030 securely without compromising the suture 2030 integrity. The gripping element 2040 may have a roughened or jagged gripping surface, or it may have a coated or polymeric gripping surface.

The suture 2030 extends through the center of the cavity base 2050 and winding pin 2060, and there may be any length of suture 2030 extending beyond the winding pin 2060. The length of suture 2030 fed into the apparatus is desirably sufficient so as to allow the winding and formation of a termination feature, while still leaving sufficient suture length to provide at least a single suture. The length of suture material may be from 5-55 inches, depending upon the desired resulting suture length after formation of the termination feature. The first end 2032 of the suture 2030 may be free of retainers or it may have retainers on its surface. In some embodiments, there may be a spool or other container 2035 holding a significant length of suture material 2030, to allow for continuous processing of sutures having termination features. In these embodiments, the suture 2030 may have alternating regions where the suture surface has retainers and regions where the suture surface is free of retainers. In such embodiments, the retainer-free sections will be used to form the termination features of the resulting sutures.

Figure 16:
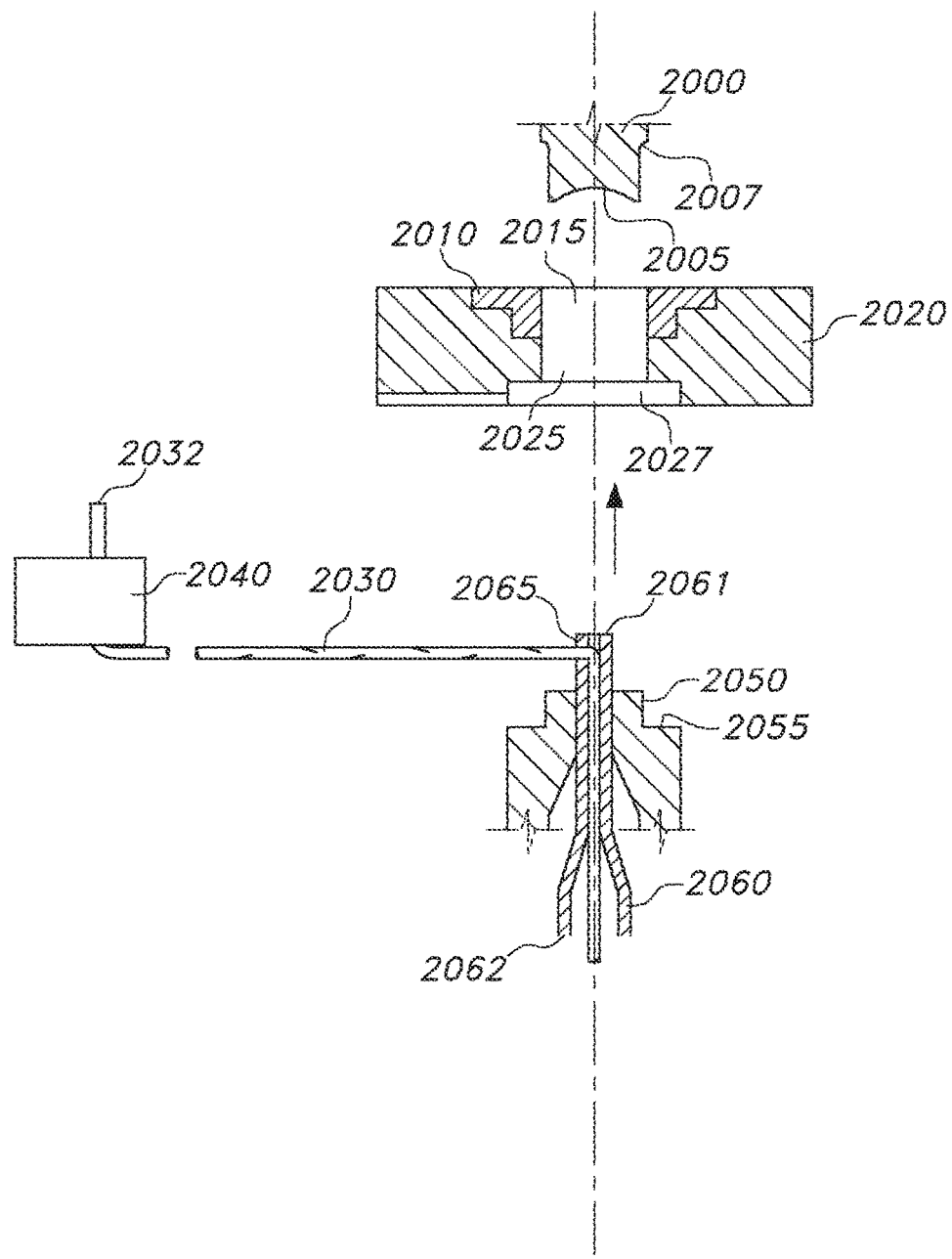
FIG. 16 depicts another step of a method of continuous processing of termination feature-containing sutures.

The method of processing termination feature-containing sutures is now described. In this method, a first step is to feed a first end 2032 of the suture 2030 through the second side 2062 of the winding pin 2060, where it can be gripped by the gripping element 2040. As seen in FIG. 16, the gripping element 2040 pulls the first end 2032 of the suture 2030 away from the axial center of the winding pin 2060, forming an approximately 90° angle of the suture 2030. Before the gripping element 2040 pulls the suture 2030, or concurrently as the gripping element 2040 pulls the suture 2030, the winding pin 2060 may be raised axially through the cavity base 2050, such that at least a portion of the first side 2061 of the winding pin 2060 sticks out through the cavity base 2050. The suture 2030 may be fed through the notch 2065. At the second end 2033 of the suture 2030, there is a sufficient length of suture 2030 remaining, so as to provide a suture length that is desired. In some embodiments, the remaining length of suture 2030 may be contained or otherwise stored, such as on a spool or reel, which can continuously feed suture 2030 to the welding apparatus. The use of a sufficient length of suture 2030 allows the suture 2030 to be pulled while maintaining at least a portion of the second end 2033 of the suture 2030 sticking out through the second side 2062 of winding pin 2060.

Figure 17:
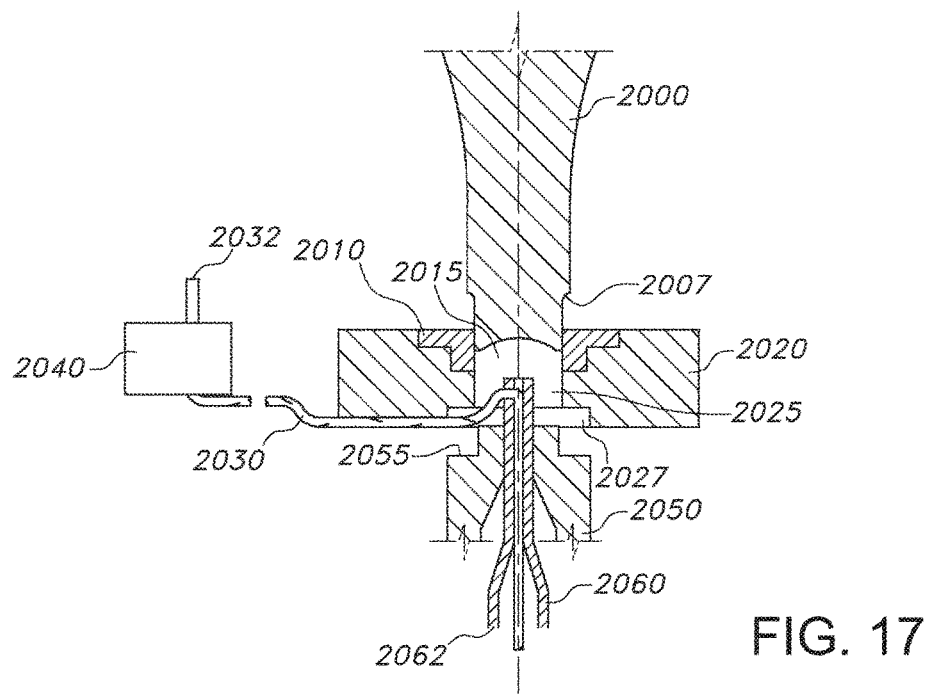
FIG. 17 depicts another step of a method of continuous processing of termination feature-containing sutures.

FIG. 17 shows the next step in the process, whereby the welding horn 2000 is moved into the central region 2015 of the insert 2010 and the winding pin 2060 and cavity base 2050 are moved into the central region of die 2020. In some embodiments, the welding horn 2000 remains stationary, while the other components move towards it. In other embodiments, the cavity base 2050 remains stationary and the other components move toward it. In yet other embodiments, the die 2020 and insert 2010 remain stationary, and the other components move toward it. Any combination of moving parts is useful in the invention.

Die 2020 may include a stepped region or flange 2027, which is sized and shaped to mate with a stepped portion 2055 of the cavity base 2050 when the two components are moved into proximity with each other. Gripping element 2040 pulls the first end 2032 of suture 2030 a sufficient length such that the suture 2030 is at least partially disposed outside the periphery of the die 2020 and/or cavity base 2050. In this configuration, suture 2030 is able to extend under the lower surface of die 2020 or, alternatively, die 2020 may include a channel through which the suture 2030 may extend. One or more of the stepped portions 2027 or 2055 may include a cutting means to sever the suture 2030 when die 2020 and cavity base 2050 are moved toward each other. In addition, the outer surface of the horn 2000 may have a flanged region 2007, which is sized and shaped to contact insert ring 2010 when the components are moved toward each other. Contact of the flanged region 2007 and the insert ring 2010 may force the welding die 2020 downward toward the cavity base 2050.

Figure 18:
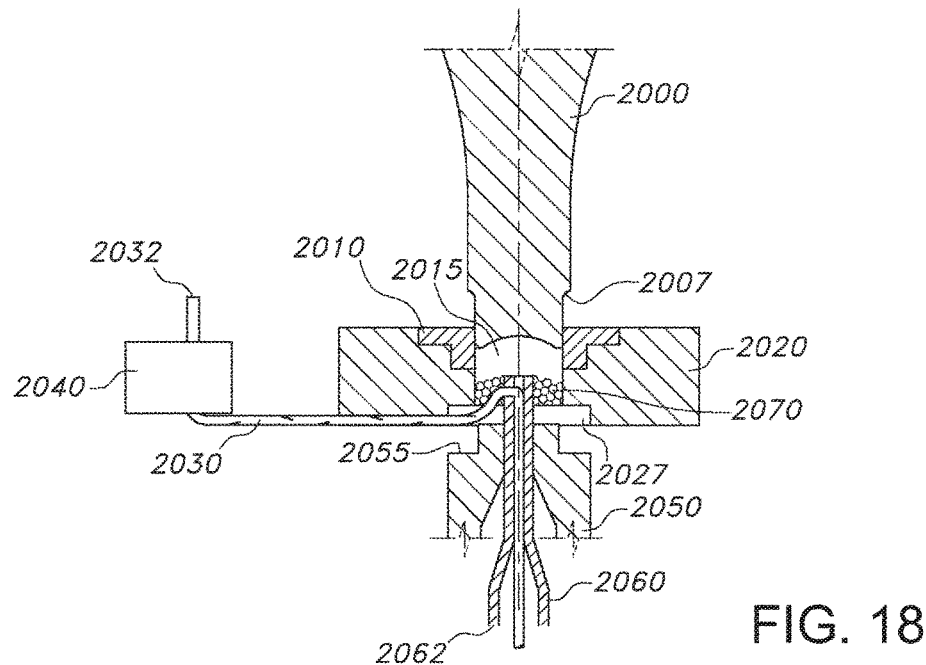
FIG. 18 depicts another step of a method of continuous processing of termination feature-containing sutures.
Figure 19:
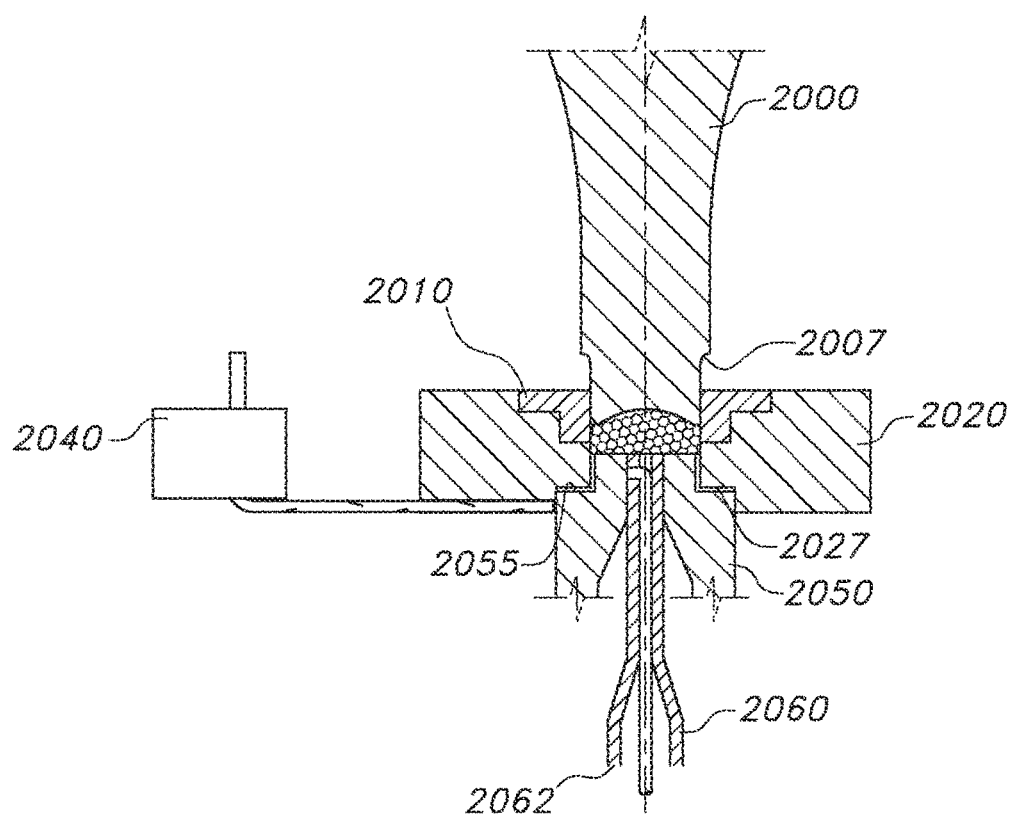
FIG. 19 depicts another step of a method of continuous processing of termination feature-containing sutures.

As can be seen in FIG. 18, once the first end 2032 of the suture 2030 has been pulled by the gripping element 2040 to a sufficient location outside the periphery of the die 2020, and the ultrasonic horn 2000 has been drawn into the interior 2015 of the insert 2010, the suture 2030 may then be wound around the outside of the winding pin 2060 to form a coil 2070. This may be achieved by rotating the gripping element 2040 or rotating the winding pin 2060. Alternatively, the winding pin 2060 may be rotatable with respect to the gripping element 2040, such that rotation of the winding pin 2060 while the gripping element 2040 retains the first end 2032 of the suture 2030 stationary causes more suture material 2030 to be pulled through the central interior of the winding pin 2060 and to become wound about the outside of the winding pin 2060. As noted above, the second end 2033 of the suture 2030 includes a length of suture 2030, which can be freely pulled into and through the winding pin 2060. The second end 2033 of the suture 2030 remains outside the winding pin 2060 and need not pass the second end 2062 of the winding pin 2060. In some embodiments, the gripping element 2040 is capable of moving closer to the winding pin 2060 during rotation of the winding pin 2060, to allow the suture material 2030 to be wound without pulling more suture material 2030 through the interior of the winding pin 2060.

The winding pin 2060 may also be capable of moving axially up or down during rotation, so as to coil the suture 2030 without tangling the suture 2030. The wound coil 2070 may be any size desired, with the understanding that the amount of wound coil 2070 will dictate the size of the resulting termination feature. In addition, the size of the suture material 2030 will dictate the number of wraps in the coil, since one thickness of the suture material 2030 may require more wraps, while other thicknesses may require less wraps. In some embodiments, the wound coil 2070 includes the suture 2030 wrapped or wound around the winding pin 2060 about 2 to about 10, and more specifically about 2.5 to about 7 times, and most specifically about 3 to about 4 times. Desirably, the wrapped coil 2070 is a tight configuration, without entangled portions or free space between adjacent coiled portions.

Once the winding step is complete and the coil 2070 is a sufficient size, the ultrasonic horn 2000 moves further into the interior 2015 of the insert ring 2010, and the tip 2005 of the horn 2000 comes into contact with at least a portion of the wound coil 2070. Again, it is noted that the horn 2000 need not necessarily move, and any of the components may be movable with respect to each other. The relative movement of the horn 2000 causes the horn flange 2007 to contact the insert ring 2010 and move the insert ring 2010 and die 2020 downward toward the cavity base 2050. This movement causes stepped regions 2027 and 2055 to come into closer proximity to each other, while the suture 2030 is contained in the space between the die 2020 and cavity base 2050, specifically between stepped regions 2027 and 2055. As the two components (die 2020 and cavity base 2050) are moved closer to each other, there is compression on the suture and this compression causes severing of the non-coiled tail of the suture 2030. As noted above, one or more stepped regions 2027 and/or 2055 may include a blade or hardened die bypassing edges for shearing or other cutting means to aid in severing the suture 2030.

Since the wound coil 2070 is held in a substantially compressed state in the region formed by the horn tip 2005 (at the upper surface of coil 2070), the cavity base 2050 (at the downward surface of coil 2070), and the die 2020 (on the outer side of the coil 2070), there is little to no unwinding of the coil 2070, although slight expansion of the coil 2070 may occur.

The winding pin 2060 is moved in a downward motion (e.g., toward the cavity base 2050), either simultaneously with the movement of the horn 2000, or immediately before the horn 2000 is moved downward. Given the compact pocket formed by the components, even when the winding pin 2060 is removed, the coil 2070 remains in a sufficiently secure state without unwinding or entangling of the suture 2030.

Once the coil 2070 is contained, energy may be applied to the coil 2070. Energy may be applied concurrently with compression if desired. Energy may be in any forms described above, including, for example, ultrasonic radiation, radiofrequency, thermal, laser, friction, and electron beam energy. Application of energy to the coil 2070 causes the polymeric material that forms the coil 2070 to become softened and take the shape of the termination feature and for abutting spiraled edges of coiled suture to fuse or bond to each other. Thus, the relative shapes of the tip 2005, cavity base 2050 and interior surface of the die 2020 will dictate the final shape of the termination feature. Once sufficient energy has been applied to the coil 2070, the energy source may be terminated and the termination feature is allowed to solidify. Desirably, the components (including horn tip 2005, die 2020, cavity base 2050) remain in the welding position for a sufficient length of time to allow the suture components to solidify or bond after the energy exposure.

Figure 20:
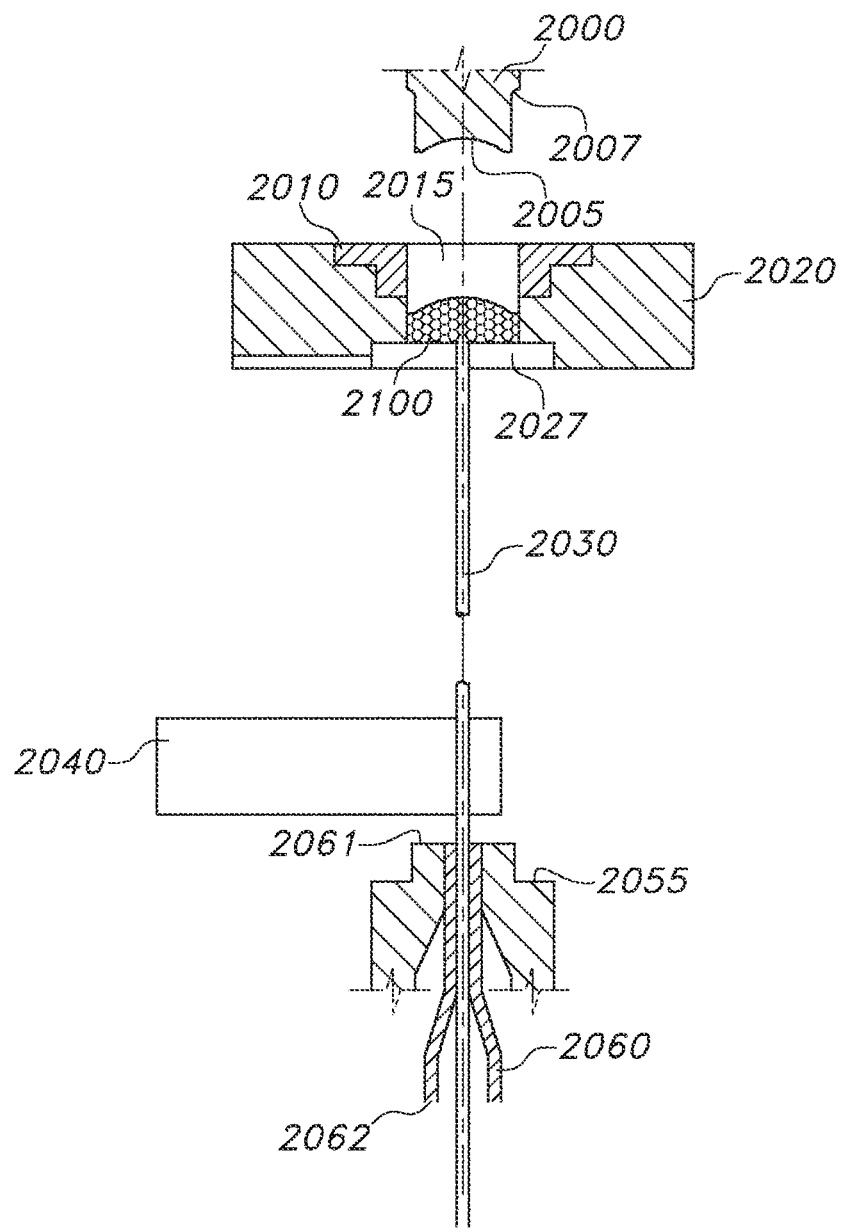
FIG. 20 depicts another step of a method of continuous processing of termination feature-containing sutures.

FIG. 20 shows the next step after sufficient solidification of the bonded termination feature 2100 is completed. Sufficient solidification refers to the termination feature 2100 being sufficiently solid so that when it is removed from a compressed area, there is little to no movement of the materials of the termination feature 2100. Some degree of expansion may be expected, given the polymeric state of the termination feature 2100, but "sufficient solidification" refers to the termination feature 2100 being in a state that its form will not freely move or components will not flow. After sufficient solidification of the termination feature 2100, the horn 2000 and/or the cavity base 2050 are moved away from each other, and the body of the suture 2030 may be pulled through the winding pin 2060 in the direction of the termination feature 2100. In embodiments where a single suture length is fed into the apparatus, removal of the remaining suture 2030 length provides a completed suture 2030. In embodiments where continuous processing is used with a length of suture housed or contained, a desired length of suture 2030 is pulled through the winding pin 2060, and the suture 2030 may be severed to provide the resulting termination-feature containing suture 2030. The length of suture 2030 used may vary depending upon the desired length of suture 2030. For example, the suture 2030 may have a length of about 15 cm to about 92 cm.

In embodiments where the suture 2030 is contained in a spool or other housing 2035, it may be desired that the gripping element 2040 engage the suture 2030 at a location between the termination feature 2100 and the winding pin 2060, and the suture 2030 be severed at a location between the termination feature 2100 and the gripping element 2040. This allows the welding process to be repeated, starting with the method described above, since the gripping element 2040 now holds the suture 2030 at a new first end 2032, and the components (horn 2000, die 2020, etc.) are moved back to their respective pre-welding positions. Again, since there is a continuous length of suture 2030 located or stored at the second end 2033, the process may be repeated until a sufficient number of termination feature-containing sutures are formed or until the spooled/stored suture 2030 is depleted. In some embodiments, one continuous length of suture material may be sufficient to form at least five termination feature-containing sutures, or at least ten termination feature-containing sutures, or at least fifty termination feature-containing sutures.

Figure 21:
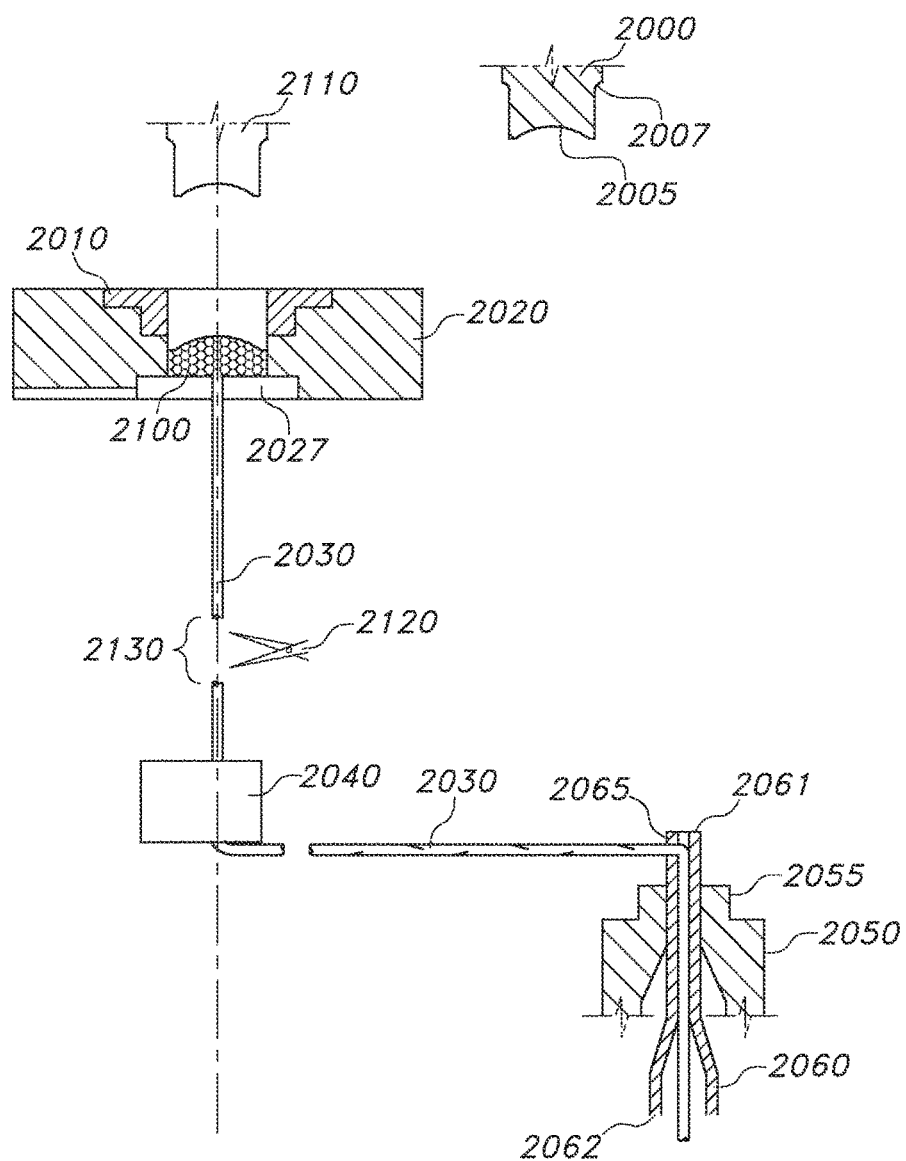
FIG. 21 depicts another step of a method of continuous processing of termination feature-containing sutures.
Figure 22:
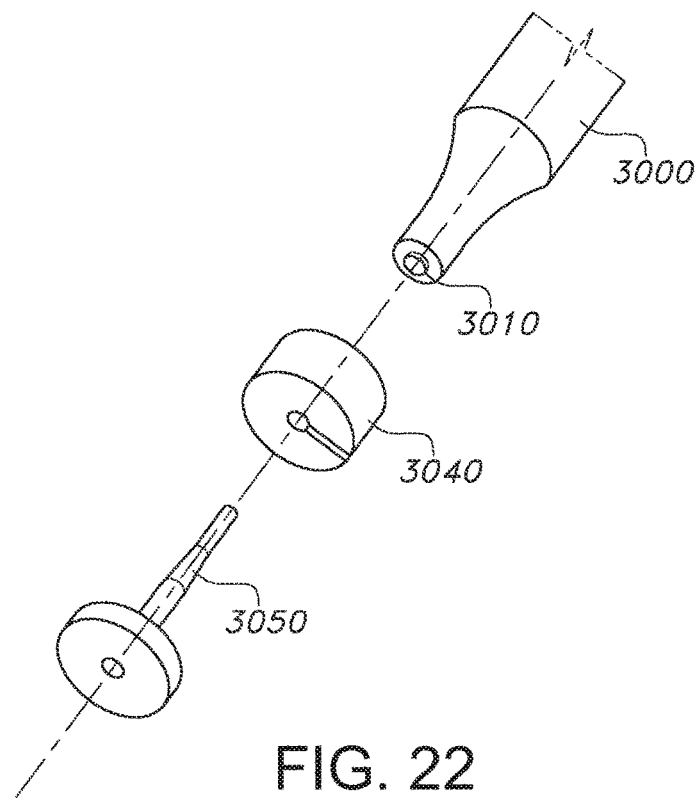
FIG. 22 depicts an alternate welding assembly for forming a termination feature in a suture.
Figure 23:
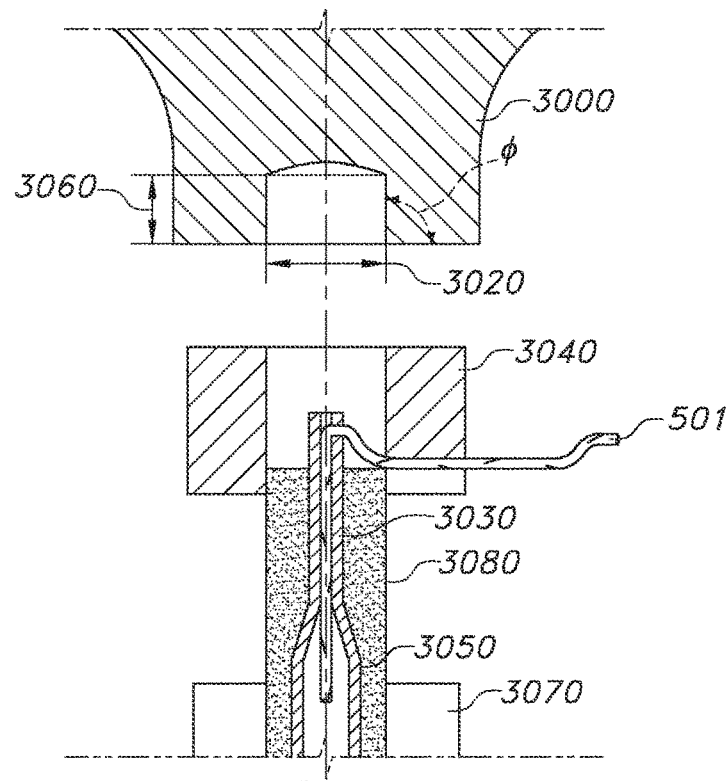
FIG. 23 shows the welding assembly of FIG. 22 as a suture is fed.

FIG. 21 depicts a method of severing the suture 2030 to form a termination feature-containing suture. As can be seen, the gripping element 2040 has gripped the suture 2030, and in this embodiment, the suture 2030 is pulled in an approximately 90° angle compared to the axis of the winding pin 2060. The suture is pulled through notch 2065 in the first end 2061 of the winding pin 2060. As can be seen, the termination feature 2100 remains within the central cavity 2025 of the die 2020. A cutter 2120 may then be used to sever the suture 2030 at any desired location. The location of the suture 2030 to be severed is based upon the desired length of a termination feature-containing suture. The cutting is desirably performed at a location 2130 between the termination feature 2100 and the gripping element 2040, and more desirably as close to the gripping element 2040 as possible. An ejector pin 2110 may be used to remove the termination feature-containing suture from the die 2020. Ejector pin 2110 may be any desired material or shape, and preferably has a sufficient surface area to contact the upper surface of the termination feature 2100 with enough force to push the termination feature 2100 out of the die 2020. Alternatively, the termination feature-containing suture can be removed from the die 2020 via any other means, including simply pulling on the suture without the use of an ejector pin 2110. The welding process can then begin again, as described above.

To summarize the method of forming a termination feature-containing suture as embodied in FIGS. 15-21, a continuous length of suture 2030 is pulled through a winding pin 2060 by a gripping element 2040. The winding pin 2060 is inserted into the center region 2025 of a die 2020, and a horn 2000 is inserted into the opposing side of the center region 2025 of the die 2020. The winding pin 2060 and/or the gripping element 2040 is rotated so as to form a coil 2070 of suture material, and the horn 2000 and cavity base 2050 are brought closer in proximity to each other and to the die 2020. The suture 2030 is severed due to forces caused by the cavity base 2050 and the die 2020, and the coil 2070 is contained in a pocket formed by the die 2020, horn tip 2005 and cavity base 2050. Winding pin 2020 may be withdrawn or it may remain in the center of the coil 2070. Energy, such as ultrasonic energy, is applied to the coil 2070, forming a termination feature 2100. Upon sufficient solidification of the termination feature 2100, the die 2020 and cavity base 2050 may be separated from each other, the suture 2030 may be gripped by the gripping element 2040. In embodiments where necessary, the suture 2030 may be severed by a cutting means 2120 at a desired length between the termination feature 2100 and the portion of the suture 2030 held by the gripping element 2040. The termination feature 2100 may be removed from the central region 2025 of the die 2020, and the resulting structure is a termination feature-containing suture. The process may be repeated with the remaining length of suture 2030 as many times as desired or until the suture 2030 is substantially depleted. Or, in embodiments where only a single length of suture 2030 is used to form a single suture 2030, the process may be repeated by inserting a second length of suture 2030 into the apparatus.

After formation of the termination feature-containing suture, the suture may be packaged in a suitable device for storage and shipment to users. In desirable embodiments, one suture should be packaged in its own secure package, and the package should be sterile (or sterilized before or after the suture is placed within the package). The package should be sized suitably to allow for ease of shipment and storage by a user, and should be capable of being opened by a user with ease and stability. It is particularly desired that the package have an open interior that is suitable to contain the suture in such a fashion that it does not become entangled and that the termination feature (e.g., 2100) is not compressed, squeezed, flattened or otherwise compromised. The package may include an interior that has guides, posts, or other features that help guide and control the length of suture when it is contained within the package. The interior of the package may also include a housing or other compartment that contains the termination feature 2100. When the package is closed with the suture contained within the package, it is particularly desired that the suture be incapable of substantial shifting or movement, where such movement or shifting could cause tangling of the suture. Particularly in embodiments where the suture is a self-retaining suture that includes a plurality of retainers on its outer surface, controlling the movement of the suture in packaging is quite important to avoid entanglement.

While the embodiments disclosed utilize unitary welding die designs, the use of split dies, similar to that used in injection and thermo forming are envisioned. Additionally, while the embodiments described herein utilize ultrasonic energy, it is contemplated that other sources of welding energy may be used, including, for example, radiofrequency, thermal, laser, friction, and electron beam energy.

With reference to FIGS. 22-26, an alternate configuration and method of forming a termination feature is described. This configuration and method includes coiling a fiber, such as a suture fiber, into a guide cylinder, and welding the fiber within the cavity formed in the horn tip. This configuration, as with that described above, includes a welding horn 3000 with a horn tip 3010, a die 3040, and a winding pin 3050. The horn tip 3010 has a diameter 3020 and open depth 3060, where the sidewalls of the horn tip have an angle measured from the horn tip of $\Phi$. The angle ($\Phi$) may be any desired, and is desirably about 90 degrees.

Winding pin 3050 may be disposed within a guide cylinder 3080, which is inserted into the central region of die 3040. As explained above, a suture fiber 501 is fed through the central interior of the winding pin 3050, where it is coiled, such as by rotation of winding pin 3050. Once the fiber 501 is coiled within the guide cylinder 3080, forming a coil 3101, the downward motion of the horn 3000 causes the guide cylinder 3080 to slide down over the winding pin 3050 which then pushes the coil 3101 into the horn tip 3010 during welding. Welding of the coil 3101 forms termination feature 3200. This method takes advantage of the known dimensions formed in the horn tip 3010 (diameter 3020, depth 3060, angle $\Phi$), and therefore provides stability of the size of the forming cavity. This method also provides benefits such as eliminating or reducing the risk of horn wear. It may also allow the guide cylinder 3080 to be made of a more cost-effective material, such as plastic, since it is not involved in the actual welding cycle. The horn tip 3010 is desirably treated, such as by polishing, to enable ejection of the resulting termination feature 3200 through the use of an after burst of energy while the horn 3000 retracts. Alternatively, the horn 3000 may have a hollow bore, in which there may be provided an ejector pin. As noted above, the suture 501 may have retainers on its outer surface, or it may be a standard, "unbarbed" suture.

Further, although various components were described as part of the method and apparatus, it is readily understood that certain elements and components can be omitted or replaced with other components, and the resulting apparatus and method will still fall under the scope of the present invention.

EXAMPLE 1

A welding die was constructed with 0.133" diameter horn tip. The inner surface of the ultrasonic horn tip was produced with a 0.010" wide flat rim surface and a 0.125" diameter spherical concave surface. The ultrasonic horn was set up on a 20 KHz Branson welder. The unit was set up with a fixed stop position set at 0.018". The welding pressure was set at 20 psi and the trigger pressure was set at 20 lbf. A 0.6 ratio reducing booster was utilized with the ultrasonic horn and the amplitude was set at 75%. The welder was set to weld on energy imparted during the cycle and was set to stop at 2.0 J of energy. The machine down speed was set at 60.

Polydioxanone (PDS) 2/0 cylindrical fiber was utilized. Approximately 3.25" of fiber was wound into the fixture and the welding cycle was initiated. The strength of the termination attachment was measured utilizing an Instron unit with a slotted metal fixture to hold the terminated end of the fiber. The fibers were pulled until the termination was broken from the fiber.

Figure 27:
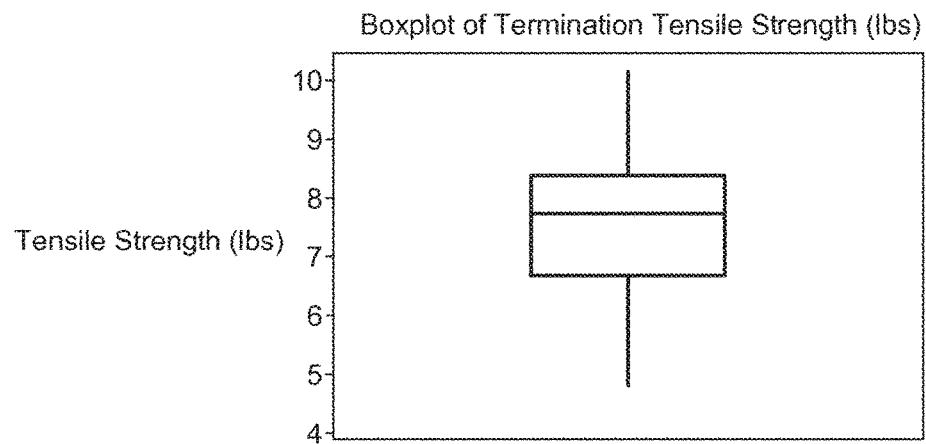
FIG. 27 depicts a box plot of termination feature tensile strength from the study in Example 1.

The results from the testing can be seen in FIG. 27, and reflected in Table 1 below:

| N | N* | Mean | SE Mean | StDev | Minimum | Q1 | Median |
|---|----|------|---------|-------|---------|-----|--------|
| 10 | 0 | 7.603 | 0.457 | 1.444 | 4.740 | 6.633 | 7.710 |

EXAMPLE 2

An ultrasonic horn was set up on a 20 KHz Branson welder. The unit was set up with a fixed stop position set at 0.018". The welding pressure was set at 25 psi and the trigger pressure was set at 20 lbf. A 0.6 ratio reducing booster was utilized with the ultrasonic horn and the amplitude was set at 70%. The welder was set to weld on energy imparted during the cycle and was set to stop at 2.1 J of energy. The machine down speed was set at 50.

Polydioxanone (PDS) 2/0 cylindrical fiber was utilized. Approximately 3.25" of fiber was wound into the fixture and the welding cycle was initiated. The strength of the termination attachment was measured utilizing an Instron unit with a slotted metal fixture to hold the terminated end of the fiber. The fibers were pulled until the termination was broken from the fiber.

Figure 28:
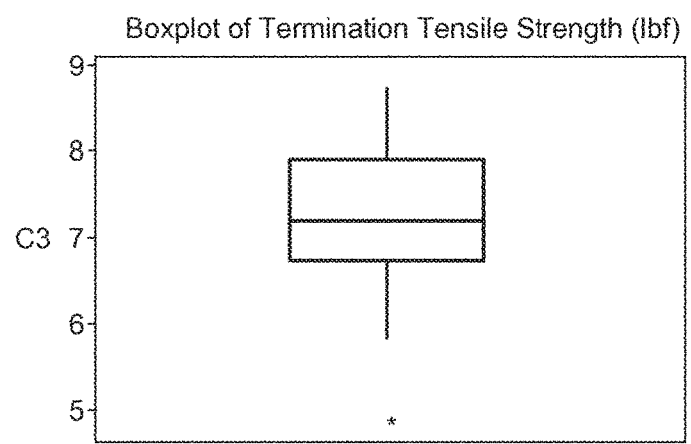
FIG. 28 depicts a box plot of termination feature tensile strength from the study in Example 2.

The results from the testing can be seen in FIG. 28, and reflected in Table 1 below:

| N | N* | Mean | SE Mean | StDev | Minimum | Q1 | Median | Q3 | Maximum |
|---|----|------|---------|-------|---------|-----|--------|-----|---------|
| 11 | 0 | 7.082 | 0.325 | 1.078 | 4.850 | 6.720 | 7.170 | 7.880 | 8.710 |

In both Example 1 and Example 2, the termination strengths, on average exceeded the USP knot tensile strength requirement established for 2/0 synthetic absorbable suture of 5.91 lbs.

What is claimed is:

1. A suture comprising:
a suture having a first end and second end and a length therebetween, wherein the length extends along a central axis;
a termination feature at the second end and extending toward the first end; and
a plurality of retainers formed on the surface of the length of suture;
wherein the termination feature comprises a coiled portion of the suture coiled about an empty interior defining a coil axis such that the coiled portion is configured to form a stable anchor for the suture without tying a knot in the suture, wherein the coiled portion includes at least first and second 360-degree loops of the suture, wherein the first and second loops are fixably welded together to form an essentially solid wall of the stable anchor, wherein the coil axis is coaxial with the central axis of the suture.

2. The suture of claim 1, wherein the termination feature has a cross section selected from the group consisting of circular, rectangular and square shaped.

3. The suture of claim 1, wherein the diameter of the termination feature is substantially perpendicular to the central axis of the suture.

4. The suture of claim 1, wherein the ratio of the diameter of the termination feature to the largest cross-sectional diameter of the suture is from about 1.1:1 to about 8:1.

5. The suture of claim 1, wherein the coiled portion has a width that is configured to extend perpendicularly relative to the length of the suture.

6. The suture of claim 1, wherein the coiled portion has a length that is configured to extend parallel relative to the length of the suture.

7. The suture of claim 1, wherein the coiled portion of the suture is configured to form a curved profile that extends parallel relative to the central axis.

8. The suture of claim 1, further comprising an insertion feature at a distal end of the suture.

9. The suture of claim 8, wherein the insertion feature comprises a needle extending distally from the distal end.

10. The suture of claim 1, wherein the termination feature is integrally formed as a unitary piece together with the suture, and wherein the welding is configured to increase tensile strength of the termination feature.

11. A suture comprising:
a. a suture including a proximal end and a distal end, wherein the suture has a length extending along a longitudinal axis;
b. a termination feature comprising a bound helical formation having a proximal end and a distal end with an open lumen formed between the proximal and distal ends of the helical formation, wherein the distal end of the termination feature is the proximal end of the suture, wherein the termination feature extends toward the distal end of the suture, wherein the suture is configured to be welded to form the termination feature without tying a knot in the termination feature, wherein the bound helical formation includes at least first and second 360-degree loops of the suture, wherein the first and second loops are fixably coupled together; and
c. a plurality of retainers extending laterally along the length of the suture.

12. The suture of claim 11, wherein the termination feature has a bulbous surface extending proximally opposite of the suture.

13. The suture of claim 11, wherein the distal end of the suture is operable to engage the opening such that the proximal end and the distal end are looped together.

14. The suture of claim 11, wherein the opening is sized and shaped greater than a cross-section of the suture.

15. The suture of claim 11, wherein the bound helical formation is defined by only a single coil.

16. The suture of claim of claim 11, wherein the distal end of the termination feature is positioned along an outer circumference of the helical formation such that the proximal end of the suture is secured to the outer circumference of the helical formation.

17. The suture of claim 11, wherein the termination feature is integrally formed as a unitary piece together with the suture, and wherein the welding is configured to increase tensile strength of the termination feature.

18. The suture of claim 11, wherein the proximal end of the suture is permanently and rigidly coupled with at least a portion of the coiled portion such that the coiled portion is configured to form a stable anchor for the suture.

19. A suture comprising:
a. a suture including a proximal end and a distal end, wherein the suture has a length extending along a longitudinal axis;
b. a termination feature at the proximal end and extending toward the distal end, wherein the termination feature comprises a coiled portion of the suture such that the suture is coiled about a central open interior to form an anchor with an open lumen, wherein the coiled portion extends parallel to the longitudinal axis, wherein the coiled portion includes at least first and second 360-degree loops of the suture, wherein the first and second loops are welded together without tying a knot in the termination feature; and
c. a plurality of retainers formed on along the length of the suture.

20. The suture of claim 19, wherein the coiled portion is configured to form a curved profile extending parallel relative to the longitudinal axis.

* * * * *